(12) United States Patent
Edwards et al.

(10) Patent No.: US 10,278,712 B2
(45) Date of Patent: *May 7, 2019

(54) ROTARY TOOL WITH IMPROVED COUPLING ASSEMBLY

(71) Applicant: Gyrus ACMI, Inc., Southborough, MA (US)

(72) Inventors: Kevin C. Edwards, Olive Branch, MS (US); Jay A. Casey, Memphis, TN (US); Peter Y. Wong, Arlington, TN (US); Jesse Conrad, Cordova, TN (US)

(73) Assignee: Gyrus ACMI, Inc., Southborough, MA (US)

( * ) Notice: Subject to any disclaimer, the term of this patent is extended or adjusted under 35 U.S.C. 154(b) by 161 days.

This patent is subject to a terminal disclaimer.

(21) Appl. No.: 15/362,320

(22) Filed: Nov. 28, 2016

(65) Prior Publication Data

US 2017/0071608 A1    Mar. 16, 2017

Related U.S. Application Data

(63) Continuation of application No. 14/700,336, filed on Apr. 30, 2015, now Pat. No. 9,504,478.

(Continued)

(51) Int. Cl.
*A61B 17/16* (2006.01)
*B23B 31/20* (2006.01)
(Continued)

(52) U.S. Cl.
CPC .......... *A61B 17/1624* (2013.01); *A61B 17/16* (2013.01); *A61B 17/162* (2013.01);
(Continued)

(58) Field of Classification Search
CPC ... A61B 17/1624; A61B 17/16; A61B 17/162; A61B 17/1622; A61B 17/1633;
(Continued)

(56) References Cited

U.S. PATENT DOCUMENTS 2,491,605 A    12/1949 Chittenden
3,576,076 A     4/1971 Weissman
(Continued)

FOREIGN PATENT DOCUMENTS

CN         2787154      6/2006
CN       201046138      4/2008
(Continued)

*Primary Examiner* — Zade Coley
*Assistant Examiner* — Jessica Weiss
(74) *Attorney, Agent, or Firm* — Pandiscio & Pandiscio

(57) ABSTRACT

A surgical device comprising: a handle assembly; a locking collar; and a set of replaceable bits that load into the handle assembly; wherein the locking collar is fully removable from the handle assembly, loads axially to a first position, and rotates between the first position and a second position; wherein, in the first position, the locking collar is free to be removed from the handle assembly and the replaceable bits are free to be loaded or unloaded from the handle assembly; wherein, in the second position, the locking collar is prevented from axial movement relative to the handle assembly and the replaceable bits are prevented from being received within, or removed from, the handle assembly; and the locking collar is guided to the first position and between the first position and the second position by a groove in the handle assembly mating with a member carried by the locking collar.

7 Claims, 23 Drawing Sheets

Related U.S. Application Data

(60) Provisional application No. 61/986,607, filed on Apr. 30, 2014.

(51) Int. Cl.
  *B23B 31/00* (2006.01)
  *B23B 31/107* (2006.01)
  *A61B 17/00* (2006.01)

(52) U.S. Cl.
  CPC ...... *A61B 17/1622* (2013.01); *A61B 17/1633* (2013.01); *B23B 31/005* (2013.01); *B23B 31/1071* (2013.01); *B23B 31/20* (2013.01); *A61B 17/1631* (2013.01); *A61B 2017/00477* (2013.01); *B23B 2231/0268* (2013.01); *B23B 2231/2078* (2013.01); *B23B 2270/16* (2013.01)

(58) Field of Classification Search
  CPC ............ A61B 17/1615; A61B 17/1617; B23B 31/005; B23B 31/1071; B23B 31/21; Y10T 279/17752; Y10T 279/17811
  USPC .................................................... 606/80–85
  See application file for complete search history.

(56) References Cited

U.S. PATENT DOCUMENTS

| | | |
|---|---|---|
| 3,672,692 A | 6/1972 | Fauth |
| 3,847,154 A * | 11/1974 | Nordin ............... A61B 17/1622 606/180 |
| 4,055,185 A | 10/1977 | Waldron |
| 4,103,663 A | 8/1978 | Elsbett et al. |
| 4,112,292 A | 9/1978 | Varvel et al. |
| 4,129,945 A | 12/1978 | Eibofner |
| 4,184,692 A | 1/1980 | Benson et al. |
| 4,260,381 A | 4/1981 | Eibofner et al. |
| 4,290,617 A | 9/1981 | Yoshida |
| 4,691,929 A | 9/1987 | Neumaier et al. |
| 4,705,038 A | 11/1987 | Sjostrom et al. |
| 4,710,079 A | 12/1987 | Smith et al. |
| 4,792,327 A | 12/1988 | Swartz |
| 4,810,139 A | 3/1989 | Regan |
| 4,818,157 A | 4/1989 | Kouvelis |
| 4,906,147 A | 3/1990 | Friesinger et al. |
| 4,940,410 A | 7/1990 | Apap et al. |
| 4,947,942 A | 8/1990 | Lightle et al. |
| 5,013,194 A | 5/1991 | Wienhold |
| 5,188,378 A | 2/1993 | Erlenkeuser |
| 5,222,956 A | 6/1993 | Waldron |
| 5,312,017 A | 5/1994 | Schroeder et al. |
| 5,363,723 A | 11/1994 | Hoffman |
| 5,372,465 A | 12/1994 | Smith |
| 5,409,322 A | 4/1995 | Horikawa et al. |
| 5,505,737 A | 4/1996 | Gosselin et al. |
| 5,531,697 A | 7/1996 | Olsen et al. |
| 5,569,256 A * | 10/1996 | Vaughn ............... A61B 17/1633 279/75 |
| 5,755,519 A | 5/1998 | Klinefelter |
| 5,888,200 A | 3/1999 | Walen |
| 5,893,851 A | 4/1999 | Umber et al. |
| 5,957,634 A | 9/1999 | Carpinetti |
| 6,037,724 A | 3/2000 | Buss et al. |
| 6,045,564 A | 4/2000 | Walen |
| 6,062,575 A | 5/2000 | Mickel et al. |
| 6,179,302 B1 | 1/2001 | Gauthier et al. |
| 6,270,087 B1 | 8/2001 | Mickel et al. |
| 6,474,656 B1 | 11/2002 | Thomas |
| 6,607,533 B2 | 8/2003 | Del Rio et al. |
| 6,733,218 B2 | 5/2004 | Del Rio et al. |
| 6,780,189 B2 | 8/2004 | Tidwell et al. |
| 6,932,382 B2 | 8/2005 | Hayes et al. |
| 6,939,213 B2 | 9/2005 | Lovchik et al. |
| 6,953,196 B1 | 10/2005 | Huang |
| 7,001,391 B2 | 2/2006 | Estes et al. |
| 7,011,661 B2 | 3/2006 | Riedel et al. |
| 7,066,940 B2 | 6/2006 | Riedel et al. |
| 7,448,870 B2 | 11/2008 | Maître |
| 7,488,332 B2 | 2/2009 | Teoh et al. |
| 7,568,866 B2 | 8/2009 | Eriksson et al. |
| 7,736,146 B2 | 6/2010 | Kuhn et al. |
| 7,871,080 B2 | 1/2011 | Marini et al. |
| 8,016,523 B2 | 9/2011 | Vasudeva et al. |
| 8,277,474 B2 | 10/2012 | Norman et al. |
| 8,319,475 B2 | 11/2012 | Choksi et al. |
| 8,465,492 B2 | 6/2013 | Estes |
| 8,529,567 B2 | 9/2013 | Garcia et al. |
| 9,113,917 B2 | 8/2015 | Del Rio et al. |
| 9,242,347 B2 | 1/2016 | Krause et al. |
| 9,414,848 B2 | 8/2016 | Edwards et al. |
| 2002/0058958 A1 | 5/2002 | Walen |
| 2003/0163134 A1 | 8/2003 | Riedel et al. |
| 2004/0122460 A1 | 6/2004 | Shores et al. |
| 2005/0096662 A1 | 5/2005 | Shores et al. |
| 2005/0167919 A1 | 8/2005 | Grant et al. |
| 2006/0043684 A1 | 3/2006 | Barber et al. |
| 2006/0085005 A1 * | 4/2006 | Kenealy, III ....... A61B 17/1615 606/80 |
| 2007/0054239 A1 | 3/2007 | Maitre |
| 2008/0195101 A1 | 8/2008 | Lechot et al. |
| 2012/0259337 A1 | 10/2012 | Del Rio et al. |
| 2013/0184692 A1 | 7/2013 | Gigon |
| 2013/0310866 A1 | 11/2013 | Belagali |
| 2014/0100567 A1 | 4/2014 | Edwards et al. |
| 2014/0155888 A1 | 6/2014 | Edwards et al. |
| 2014/0277036 A1 | 9/2014 | Flynn et al. |
| 2015/0313612 A1 | 11/2015 | Edwards et al. |

FOREIGN PATENT DOCUMENTS

| | | | |
|---|---|---|---|
| CN | 201710409 | 1/2011 | |
| CN | 101711129 | 7/2012 | |
| DE | 4103663 | 8/1992 | |
| JP | 2007-521896 | 8/2007 | |
| JP | 2017-500971 | 1/2017 | |
| WO | WO 98/05261 | 2/1998 | |
| WO | WO 2006/104929 | 10/2006 | |
| WO | WO 2012/138338 | 10/2012 | |
| WO | WO 2014003848 A1 * | 1/2014 | ............ A61B 17/32 |

\* cited by examiner

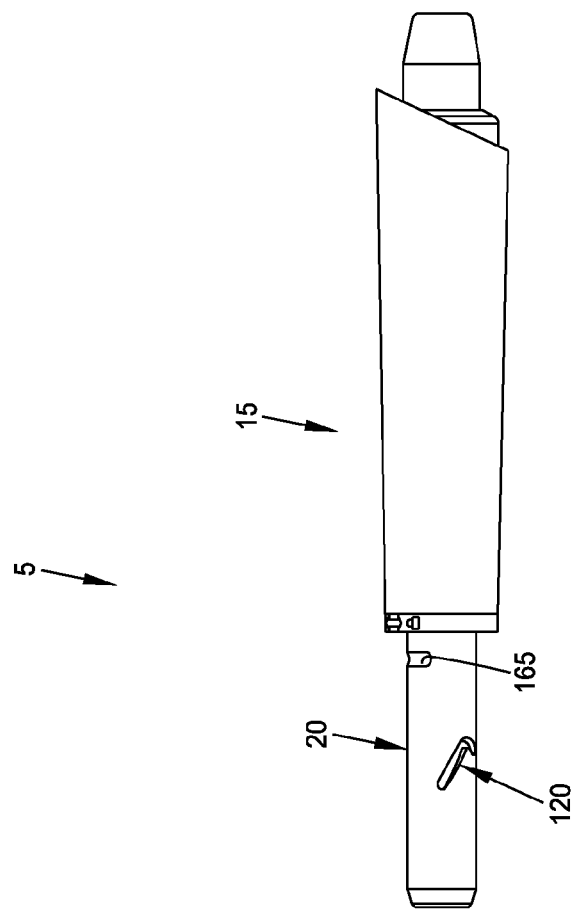
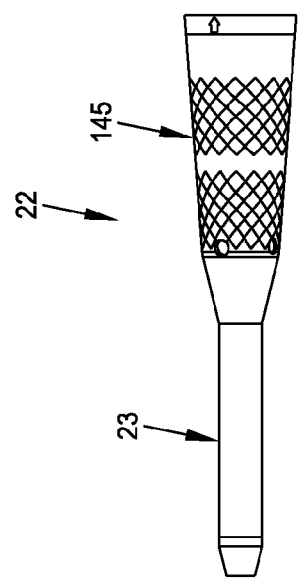
FIG. 2

ROTARY TOOL WITH IMPROVED COUPLING ASSEMBLY

REFERENCE TO PENDING PRIOR PATENT APPLICATIONS

This patent application is a continuation of pending prior U.S. patent application Ser. No. 14/700,336, filed Apr. 30, 2015 by Gyrus ACMI, Inc., d.b.a. Olympus Surgical Technologies America and Kevin C. Edwards et al. for ROTARY TOOL WITH IMPROVED COUPLING ASSEMBLY, which claims benefit of prior U.S. Provisional Patent Application Ser. No. 61/986,607, filed Apr. 30, 2014 by Gyrus ACMI, Inc., d.b.a. Olympus Surgical Technologies America and Kevin C. Edwards et al. for ROTARY TOOL WITH IMPROVED COUPLING.

The two (2) above-identified patent applications are hereby incorporated herein by reference.

FIELD OF THE INVENTION

This invention relates to surgical apparatus and procedures in general, and more particularly to rotary tools of the sort used to drive working elements such as drill bits and burrs.

BACKGROUND OF THE INVENTION

In many surgical procedures, it is necessary or desirable to drill or abrade an object, e.g., bone. In these situations, it is common to provide a rotary tool comprising a handle assembly having a high speed motor, and a coupling assembly at the distal end of the handle assembly for releasably connecting a working element (e.g., a drill bit or burr) to the high speed motor, such that the working element (e.g., the drill bit or burr) can be turned by the high speed motor and then used for the desired purpose (e.g., drilling or abrading bone).

The present invention provides a novel coupling assembly for releasably connecting a working element (e.g., a drill bit or burr) to a high speed motor of a handle assembly of a rotary tool.

For purposes of clarity of description, the present invention will sometimes hereinafter be discussed in the context of a high speed drill bit or burr, however, it should be appreciated that the present invention is also applicable to other working elements, e.g., a dental polishing head, etc.

SUMMARY OF THE INVENTION

The present invention comprises the provision and use of a novel coupling assembly for releasably connecting a working element (e.g., a drill bit or burr) to a high speed motor of a handle assembly of a rotary tool.

For purposes of clarity of description, the present invention will sometimes hereinafter be discussed in the context of a high speed drill bit or burr, however, it should be appreciated that the present invention is also applicable to other working elements, e.g., a dental polishing head, etc.

In one preferred form of the invention, there is provided a surgical device comprising:
a handle assembly;
a locking collar; and
a set of replaceable bits that load along an axis into said handle assembly;
wherein said locking collar is fully removable from said handle assembly, said locking collar loads axially to a first position, and said locking collar rotates between said first position and a second position;
wherein, in said first position, said locking collar is free to be axially removed from said handle assembly and said replaceable bits are free to be loaded or unloaded from said handle assembly;
wherein, in said second position, said locking collar is prevented from axial movement relative to said handle assembly and said replaceable bits are prevented from being received within, or removed from, said handle assembly; and
said locking collar is guided to said first position and between said first position and said second position by a groove in said handle assembly mating with a member carried by said locking collar.

In another preferred form of the invention, there is provided a surgical device comprising:
a handle assembly, said handle assembly comprising:
a collet sleeve, said collet sleeve comprising at least one opening extending radially through said collet sleeve;
a hollow housing;
at least one canted cam slot formed in said hollow housing, said at least one canted cam slot having a first end and a second end;
a biasing collar, said biasing collar comprising at least one biasing collar engagement element, said at least one biasing collar engagement element extending through said at least one canted cam slot and extending outwardly from the outer surface of said hollow housing, said biasing collar being configured to move between a first biasing collar position and a second biasing collar position;
a cam element, said cam element being configured to move between a first cam element position and a second cam element position;
a biasing element, said biasing element biasing said cam element towards said second cam element position; and
at least one locking element, said at least one locking element being configured to move in said at least one opening in said collet sleeve; and
a locking collar, wherein said locking collar is fully removable from said handle assembly, and further wherein said locking collar is configured to directly engage the portion of said at least one biasing collar engagement element which extends outwardly from the outer surface of said hollow housing and is configured to rotate between a first locking collar position and a second locking collar position;
wherein, when said locking collar is in its first locking collar position, said at least one biasing collar engagement element is engaged with said locking collar and is driven to said first end of said at least one canted cam slot, causing said biasing collar to be driven to said first biasing collar position, in which position said biasing collar urges said cam element to said first cam element position, and further wherein, with said cam element in said first cam element position, said at least one locking element is free to move radially outward in said at least one opening of said collet sleeve; and
wherein rotation of said locking collar from said first locking collar position to said second locking collar position causes said at least one biasing collar engagement element to be driven to said second end of said at least one canted cam slot, and said biasing collar is driven to said second biasing collar position, such that said biasing collar is retracted beyond the travel of said cam element, allowing said biasing element to drive said cam element to its said second cam element position, in which position said at least one locking element is driven into said at least one opening in said collet sleeve so that a portion of said at least one locking element extends radially inward from the inner wall of said collet sleeve.

In another preferred form of the invention, there is provided a method for securing a working element to a surgical device, said method comprising:

providing a surgical device comprising:
  a handle assembly, said handle assembly comprising:
    a collet sleeve, said collet sleeve comprising at least one opening extending radially through said collet sleeve;
    a hollow housing;
    at least one canted cam slot formed in said hollow housing, said at least one canted cam slot having a first end and a second end;
    a biasing collar, said biasing collar comprising at least one biasing collar engagement element, said at least one biasing collar engagement element extending through said at least one canted cam slot and extending outwardly from the outer surface of said hollow housing, said biasing collar being configured to move between a first biasing collar position and a second biasing collar position;
    a cam element, said cam element being configured to move between a first cam element position and a second cam element position;
    a biasing element, said biasing element biasing said cam element towards said second cam element position; and
    at least one locking element, said at least one locking element being configured to move in said at least one opening in said collet sleeve; and
    a locking collar, wherein said locking collar is fully removable from said handle assembly, and further wherein said locking collar is configured to directly engage the portion of said at least one biasing collar engagement element which extends outwardly from the outer surface of said hollow housing and is configured to rotate between a first locking collar position and a second locking collar position;
  wherein, when said locking collar is in its first locking collar position, said at least one biasing collar engagement element is engaged with said locking collar and is driven to said first end of said at least one canted cam slot, causing said locking collar to be driven to said first locking collar position, in which position said locking collar urges said cam element to said first cam element position, and further wherein, with said cam element in said first cam element position, said at least one locking element is free to move radially outward in said at least one opening in said collet sleeve; and
  wherein rotation of said locking collar from said first locking collar position to said second locking collar position causes said at least one biasing collar engagement element to be driven to said second end of said at least one canted cam slot, and said biasing collar is driven to said second biasing collar position, such that said biasing collar is retracted beyond the travel of said cam element, allowing said biasing element to drive said cam element to its said second cam element position, in which position said at least one locking element is driven into said at least one opening in said collet sleeve so that a portion of said at least one locking element extends radially inward from the inner wall of said collet sleeve;

rotating said locking collar so as to cause said biasing collar to move said cam element into said first cam element position;

positioning the shaft of a working element in said collet sleeve; and rotating said locking collar so as to cause said biasing collar to move so as to allow said cam element to assume its second cam element position.

In another preferred form of the invention, there is provided a surgical device comprising:
  a handle assembly comprising a rotatable drive shaft;
  a removable handle assembly adapter for connection to said handle assembly, said removable handle assembly adapter comprising a rotatable transmission shaft for connection to said rotatable drive shaft of said handle assembly; and
  a removable nosepiece assembly for connection to said removable handle assembly adapter and for selectively securing the shaft of a working element to said rotatable transmission shaft of said removable handle assembly adapter;
  wherein said removable handle assembly adapter and said removable nosepiece assembly each comprise a locking collar; and
  wherein said removable handle assembly adapter and said handle assembly each comprise a connector assembly, said connector assembly comprising:
    a housing comprising an opening;
    a collet sleeve disposed within said opening and connected to an input shaft, said collet sleeve comprising a lumen for receiving an output shaft;
    a locking element movable relative to said collet sleeve between (i) a locked position in which said output shaft is secured to said collet sleeve, and (ii) an unlocked position in which said output shaft is not secured to said collet sleeve; and
    a cam element movable relative to said collet sleeve between (i) a first position in which said locking element is free to assume its said unlocked position, and (ii) a second position in which said cam element cams said locking element into said locked position;
  such that movement of said locking collar causes said cam element to move between said first position and said second position.

In another preferred form of the invention, there is provided a kit comprising:
  a handle assembly comprising a rotatable drive shaft;
  a removable nosepiece assembly; and
  a set of replaceable bits;
  wherein said removable nosepiece assembly is configured for mounting to said handle assembly and for accepting a replaceable bit so that said replaceable bit is connected to said rotatable drive shaft; and
  a removable handle assembly adapter having a rotatable shaft, said removable handle assembly adapter being configured at one end for mounting to said handle assembly and being configured at another end for receiving said nosepiece assembly so that said replaceable bit is connected to said rotatable drive shaft via said rotatable shaft of said removable handle assembly.

In another preferred form of the invention, there is provided a surgical device comprising:
  a handle assembly comprising a powered drive shaft; and
a first connector assembly;
  a removable nosepiece assembly for connection to said handle assembly, said removable nosepiece assembly comprising:
    a first shaft with a first shaft engagement portion for connection to said powered drive shaft of said handle assembly;
    a second shaft with a second shaft engagement portion for connection to the shaft of a working element; and
    a second connector assembly;
  wherein each of said first and second connector assemblies comprises:
    a housing comprising an opening;
    a collet sleeve disposed within said opening and connected to an input shaft, said collet sleeve comprising a lumen for receiving an output shaft;
    a locking element movable relative to said collet sleeve between (i) a locked position in which the output shaft is secured to said collet sleeve, and (ii) an unlocked position in which the output shaft is not secured to said collet sleeve;
    a cam element movable relative to said collet sleeve between (i) a first position in which said locking element is free to assume its said unlocked position, and (ii) a second position in which said cam element cams said locking element into said locked position; and
    a locking collar mounted to said housing such that rotation of said locking collar causes said cam element to move into said second position.

In another preferred form of the invention, there is provided a surgical device comprising:
  a handle assembly comprising a rotatable drive shaft;
  a removable handle assembly adapter for connection to said handle assembly, said removable handle assembly adapter comprising a rotatable transmission shaft for connection to said rotatable drive shaft of said handle assembly; and
  a removable nosepiece assembly for connection to said removable handle assembly adapter and for selectively securing the shaft of a working element to said rotatable transmission shaft of said removable handle assembly adapter;
  wherein at least one of said removable handle assembly adapter and said removable nosepiece assembly comprises a removable locking collar; and
  wherein at least one of said removable handle assembly adapter and said handle assembly comprises a connector assembly, said connector assembly comprising:
    a housing comprising an opening and a canted slot;
    a collet sleeve disposed within said opening and connected to an input shaft, said collet sleeve comprising a lumen for receiving an output shaft;
    a locking element radially movable relative to said collet sleeve between (i) a locked position in which said output shaft is secured to said collet sleeve, and (ii) an unlocked position in which said output shaft is not secured to said collet sleeve;
    a cam element longitudinally movable relative to said collet sleeve between (i) a first position in which said locking element is free to assume its said unlocked position, and (ii) a second position in which said cam element cams said locking element into said locked position, said cam element being yieldably biased into said second position;
    a biasing collar for biasing said cam element into said first position; and
    an element extending through said canted slot and secured to said biasing collar and said locking collar, such that rotation of said locking collar causes said element to move within said canted slot, whereby to cause said biasing collar to move said cam element between said second position and said first position.

In another preferred form of the invention, there is provided a method for securing a replaceable bit to a handpiecesurgical device, said method comprising:
  providing a surgical device comprising:
    a handpiece handle comprising a powered rotatable drive shaft;
    a removable handpiece handle assembly adapter for connection to said handpiecehandle assembly, said removable handpiece handle assembly adapter comprising a rotatable transmission shaft for connection to said powered rotatable drive shaft of said handpiecehandle assembly; and
    a removable coupling nosepiece assembly for connection to said removable handpiece handle assembly adapter and for selectively securing the shaft of a working element to said rotatable transmission shaft of said removable handpiece handle assembly adapter;
    wherein at least one of said removable handle assembly adapter and said removable nosepiece assembly comprises a removable locking collar; and
    wherein at least one of said removable handpiece handle assembly adapter and said handpiece handle assembly comprises a connector assembly, said connector assembly comprising:
      a housing comprising an opening and a canted slot;
      a collet sleeve disposed within said opening and connected to an input shaft, said collet sleeve comprising a lumen for receiving an output shaft;
      a locking element radially movable relative to said collet sleeve between (i) a locked position in which the said output shaft is secured to said collet sleeve, and (ii) an unlocked position in which the said output shaft is not secured to said collet sleeve;
      a cam element longitudinally movable relative to said collet sleeve between (i) a first position in which said locking element is free to assume its said unlocked position, and (ii) a second position in which said cam element cams said locking element into said locked position, said cam element being yieldably biased into said second position;
      a biasing collar for biasing said cam element into said first position;
      a locking collar removably mounted to said housing; and
      an element extending through said helical canted slot and secured to said biasing collar and said locking collar, such that rotation of said locking collar causes said element to move within said helical canted slot, whereby to cause said biasing collar to move said cam element into said first position;
  rotating said locking collar so as to cause said biasing collar to move said cam element into said first position;
  positioning a shaft in said lumen of said collet sleeve; and
  rotating said locking collar so as to cause said biasing collar to move within said housing so as to allow said cam element to assume its second position.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 2 is an exploded schematic view of the novel rotary tool shown in FIG. 1;

DETAILED DESCRIPTION OF THE PREFERRED EMBODIMENTS

The present invention comprises the provision and use of a novel coupling assembly for releasably connecting a working element (e.g., a drill bit or burr) to a high speed motor of a handle assembly of a rotary tool.

For purposes of clarity of description, the present invention will sometimes hereinafter be discussed in the context of a high speed drill bit or burr, however, it should be appreciated that the present invention is also applicable to other working elements, e.g., a dental polishing head, etc.

Figure 1:
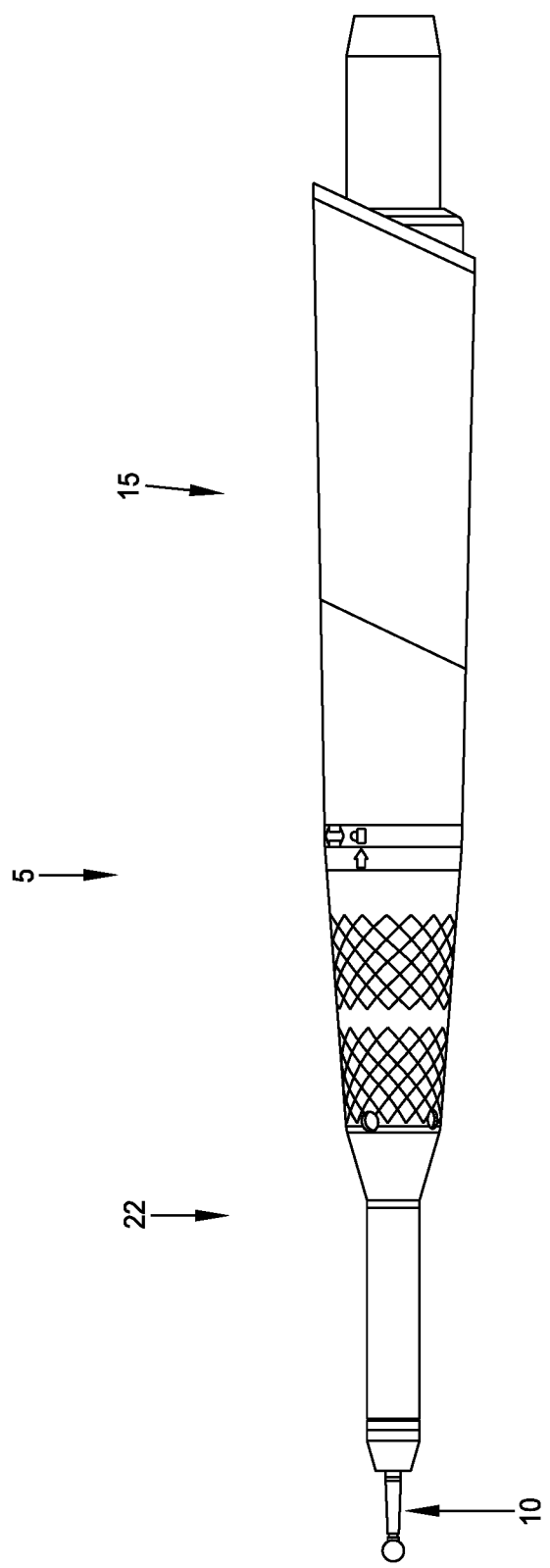
FIG. 1 is a schematic view showing a novel rotary tool provided in accordance with the present invention.
Figure 3:
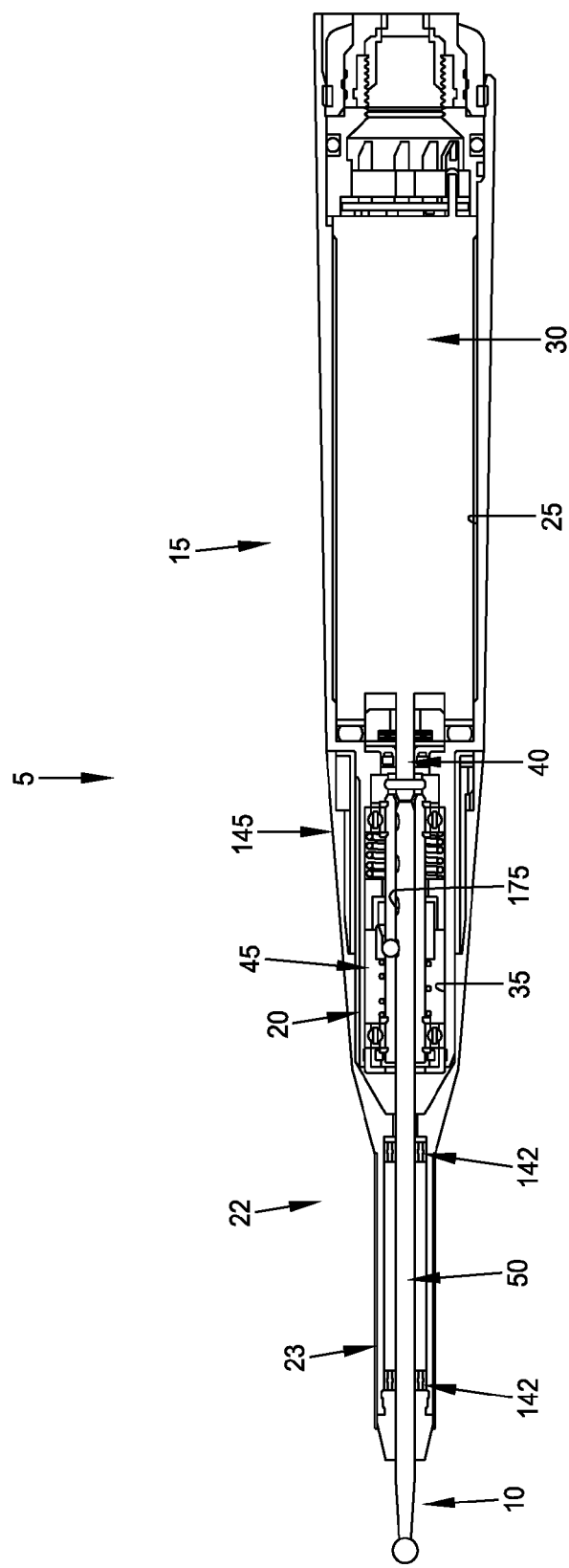
FIG. 3 is a sectional schematic view of the novel rotary tool shown in FIG. 1.

Looking first at FIGS. 1-3, there is shown a novel rotary tool 5 for turning a working element (e.g., a drill bit or burr) 10. Rotary tool 5 generally comprises a handle assembly 15 having a distal mount 20 extending distally therefrom, and a nosepiece assembly 22 mountable to, and fully removable from, distal mount 20 of handle assembly 15. Nosepiece assembly 22 comprises a distal tip 23 for rotatably supporting working element 10.

More particularly, handle assembly 15 comprises a cavity 25 having a high speed motor 30 (e.g., an 80,000 rpm motor) disposed therein. Distal mount 20 of handle assembly 15 comprises a cavity 35. Cavity 35 in distal mount 20 may be aligned with cavity 25 in handle assembly 15. High speed motor 30 turns a shaft 40 which extends into cavity 35 in distal mount 20.

A coupling assembly 45, generally disposed in distal mount 20 of handle assembly 15, releasably receives the shaft 50 of working element 10 and selectively couples the shaft of the working element to high speed motor 30.

Figure 4:
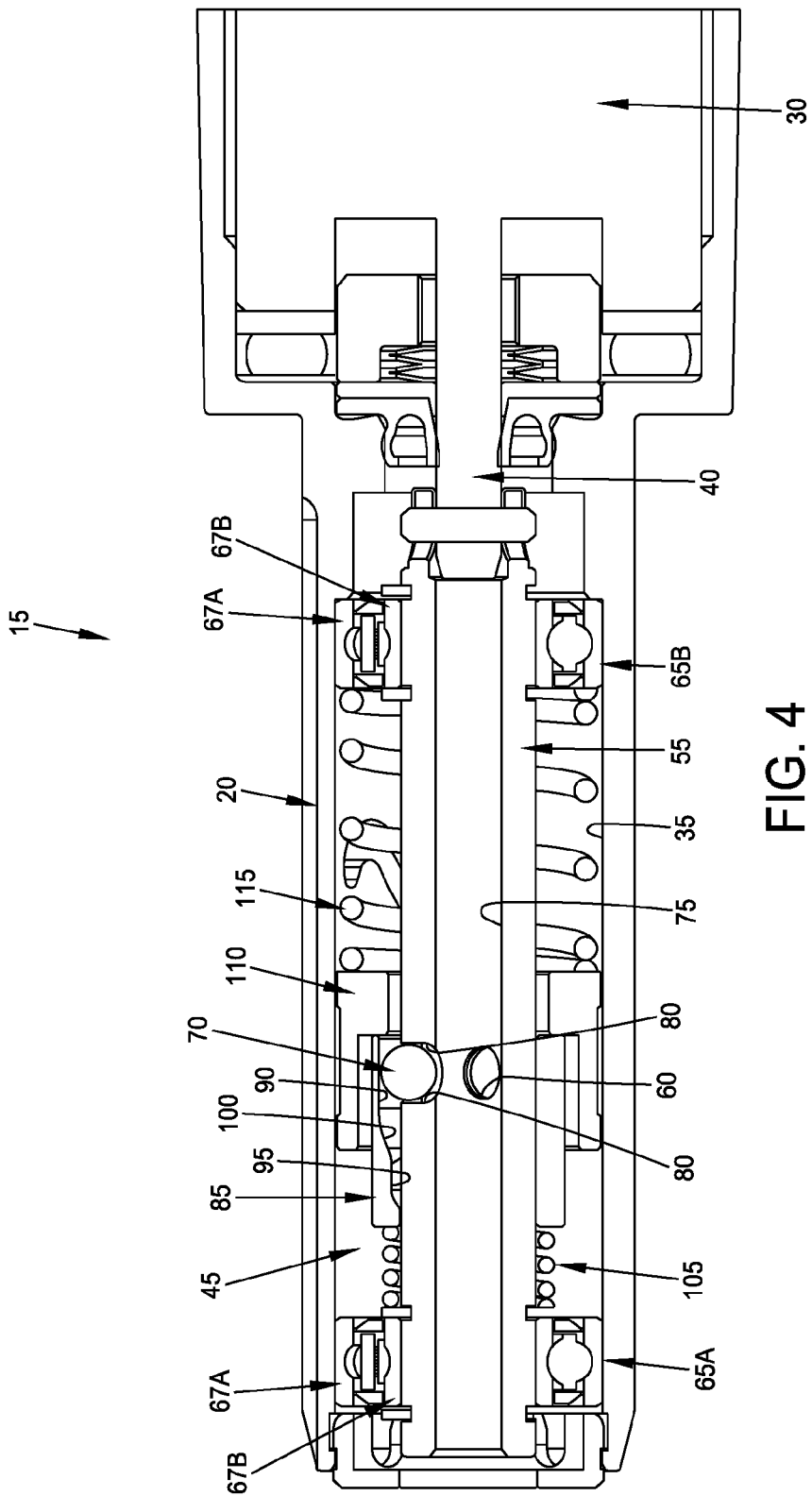
FIGS. 4-13 are schematic views showing construction details of the novel rotary tool shown in FIG. 1.

More particularly, and looking now at FIG. 4, coupling assembly 45 generally comprises a collet sleeve 55 which is secured to shaft 40 of high speed motor 30. Collet sleeve 55 is preferably connected to shaft 40 of high speed motor 30 by a universal joint or a similar type of connector so as to minimize alignment and vibration issues. Collet sleeve 55 is sized to receive shaft 50 of working element 10 (FIG. 3), and comprises at least one opening 60 extending through the side wall of collet sleeve 55. In one preferred form of the invention, collet sleeve 55 comprises three openings 60 extending through the side wall of collet sleeve 55. The three openings 60 may be equally-circumferentially spaced about the longitudinal axis of collet sleeve 55. Collet sleeve 55 is rotatably mounted within cavity 35 of distal mount 20, e.g., by a plurality of bearings 65. In this way, when shaft 40 of high speed motor 30 is turned, collet sleeve 55 is also turned. In one preferred form of the invention, there is provided a distal bearing 65A comprising an inner race 66A secured to collet sleeve 55 and an outer race 67A secured to distal mount 20; and a proximal bearing 65B comprising an inner race 66B secured to collet sleeve 55 and an outer race 67B secured to distal mount 20.

In order for coupling assembly 45 to releasably secure shaft 50 of working element 10 to collet sleeve 55, coupling assembly 45 also comprises at least one collet ball 70 (or other locking element) which is disposed in the at least one opening 60 of collet sleeve 55 (where three openings 60 are provided in collet sleeve 55, three collet balls 70 may be provided, with one collet ball 70 being disposed in each opening 60). Note that the at least one opening 60 of collet sleeve 55 is configured so that the at least one collet ball 70 can protrude into the central lumen 75 of collet sleeve 55, but the at least one collet ball 70 cannot pass completely into central lumen 75 of collet sleeve 55 due to the provision of shoulders 80 at the innermost points of the at least one opening 60. In an alternative construction, the at least one opening 60 comprises at least one tapered opening, in which case shoulders 80 are replaced by the tapering side wall of the at least one tapered opening.

A cam element 85 is disposed about collet sleeve 55. Cam element 85 comprises a first surface 90 and a second surface 95, with a transition surface 100 disposed therebetween. As will hereinafter be discussed, when first surface 90 of cam element 85 is aligned with the at least one collet ball 70, the at least one collet ball 70 is free to move radially outward to the extent necessary so that the at least one collet ball 70 does not intrude into central lumen 75 of collet sleeve 55; at the same time, when first surface 90 of cam element 85 is aligned with the at least one collet ball 70, first surface 90 will prevent the at least one collet ball 70 from completely exiting the at least one opening 60, so that the at least one collet ball 70 will remain connected to collet sleeve 55. As a result, when first surface 90 of cam element 85 is aligned with the at least one collet ball 70, first surface 90 will limit radially-outward movement of the at least one collet ball 70 and prevent the at least one collet ball 70 from "completely falling out of" the at least one opening 60 and becoming loose within cavity 35. However, when cam element 85 is moved proximally (e.g., under the power of a spring 105 or other biasing element), transition surface 100 of cam element 85, and then second surface 95 of cam element 85, will engage the at least one collet ball 70, whereby to cam the at least one collet ball 70 radially inwardly, into central lumen 75 of collet sleeve 55 (whereby to secure the shaft 50 of a working element 10 to collet sleeve 55).

It should be appreciated that cam element 85 and spring 105 rotate in conjunction with collet sleeve 55, with spring 105 extending between the inner race 66A of distal bearing 65A and the distal end of cam element 85.

Figure 5:
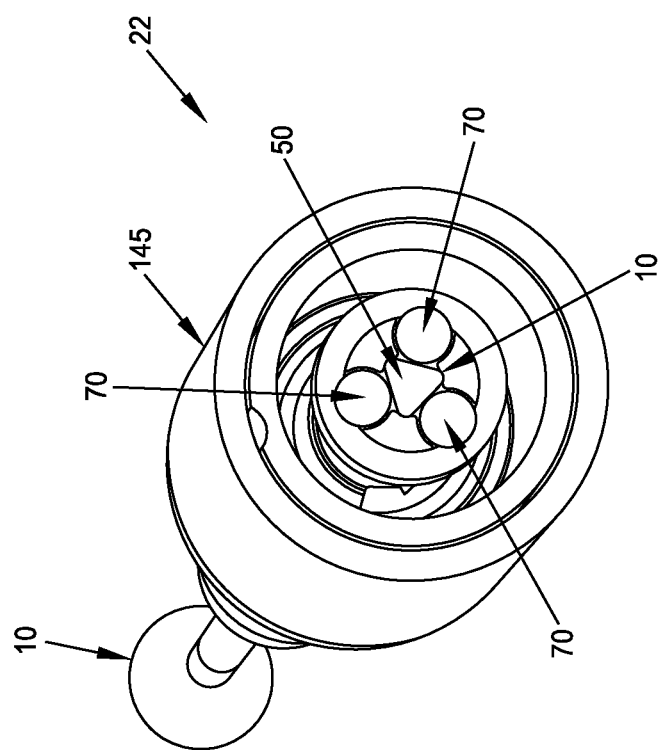

Note that in one preferred construction, three collet balls 70 are provided, one for each of three equally-circumferentially-spaced openings 60, and shaft 50 of working element 10 has a triangular cross-section (FIG. 5), whereby to provide a secure, stable connection between coupling assembly 45 and the shaft 50 of a working element 10 when the three collet balls 70 are forced radially inwardly into contact with the shaft 50 of a working element. Note also that, if desired, the at least one collet ball 70 can be replaced by at least one element having a different configuration, e.g., the at least one collet ball 70 may be replaced by at least one pin, by at least one finger, etc.

A biasing collar 110 (FIG. 4) is provided to selectively bias cam element 85 distally, against the power of its associated spring 105. More particularly, biasing collar 110 is itself biased distally by a spring 115 (or other biasing element), such that when biasing collar 110 is unconstrained (see below), biasing collar 110 will engage the proximal end of cam element 85 so as to force cam element 85 distally, such that first surface 90 of cam element 85 is aligned with the at least one collet ball 70 (FIG. 4). However, when biasing collar 110 is forced proximally (see below), against the power of spring 115, cam element 85 is free to move proximally under the power of its associated spring 105, so that transition surface 100 of cam element 85, and then second surface 95 of cam element 85, engage the at least one collet ball 70, whereby to cam the at least one collet ball 70 radially inwardly, into central lumen 75 of collet sleeve 55. In one preferred form of the invention, biasing collar 110 rides against the inner surface of mount 20 of handle assembly 15.

Note that spring 115 extends between the outer race 67B of proximal bearing 65B and the proximal end of biasing collar 110.

Note also that biasing collar 110 and spring 115 do not rotate with collet sleeve 55 when collet sleeve 55 is rotated by high speed motor 30 of handle assembly 15, as will hereinafter be discussed.

Means are provided for (i) selectively holding biasing collar 110 proximally spaced from cam element 85 (even when cam element 85 is biased proximally under the power of spring 105) so that frictional forces are not created between cam element 85 (which rotates with shaft 40 of high speed motor 30) and biasing collar 110 (which does not rotate with shaft 40 of high speed motor 30), and (ii) allowing the user to force biasing collar 110 proximally, against the power of spring 115, so that cam element 85 can move proximally under the power of its associated spring 105 and thereby drive the at least one collet ball 70 into central lumen 75 of collet sleeve 55, whereby to lock the shaft 50 of a working element 10 within coupling assembly 45.

Figure 6:
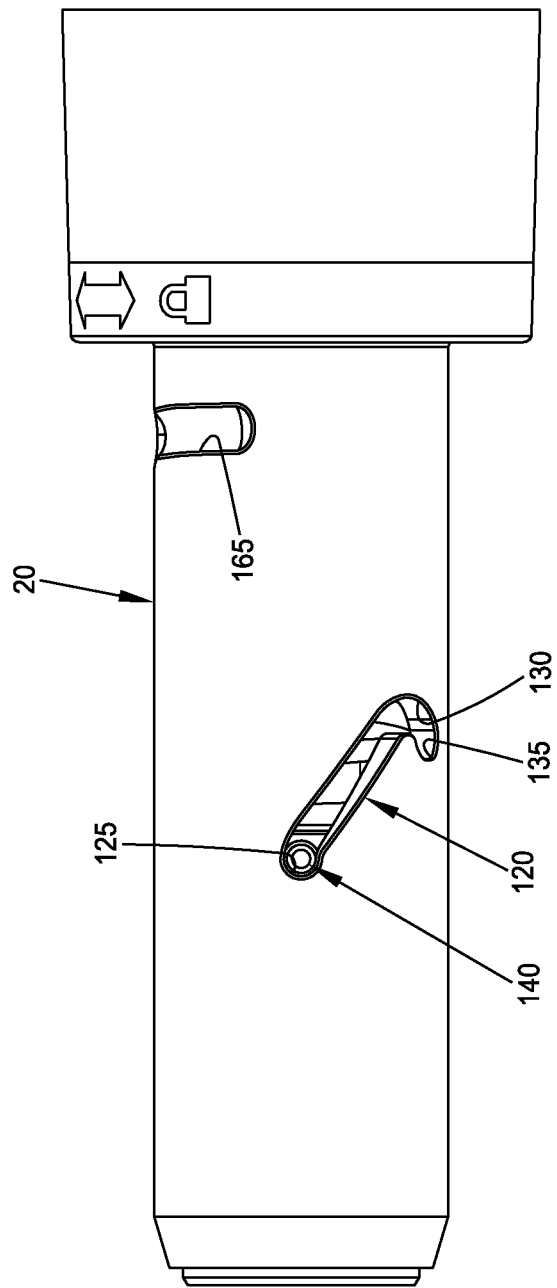
Figure 7:
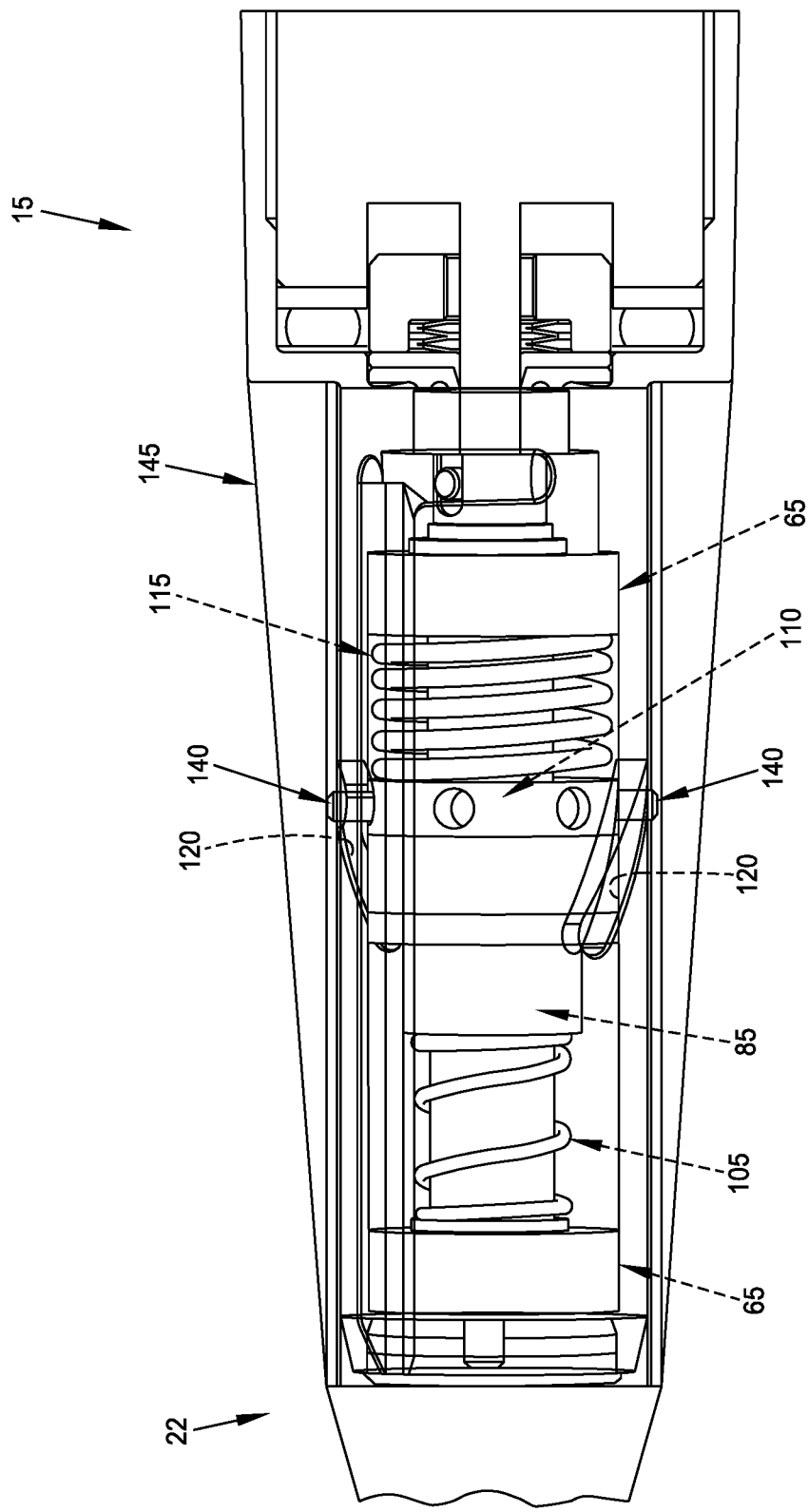
Figure 8:
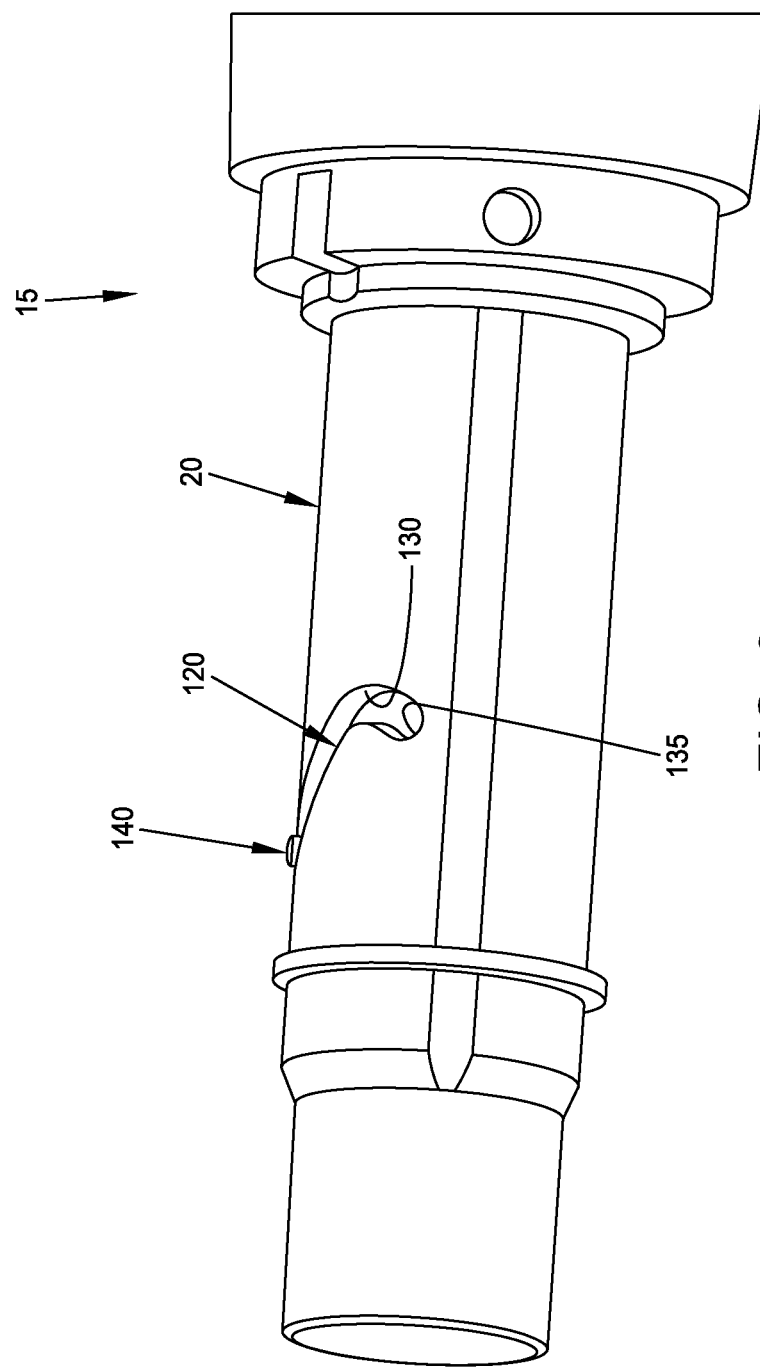
Figure 9:
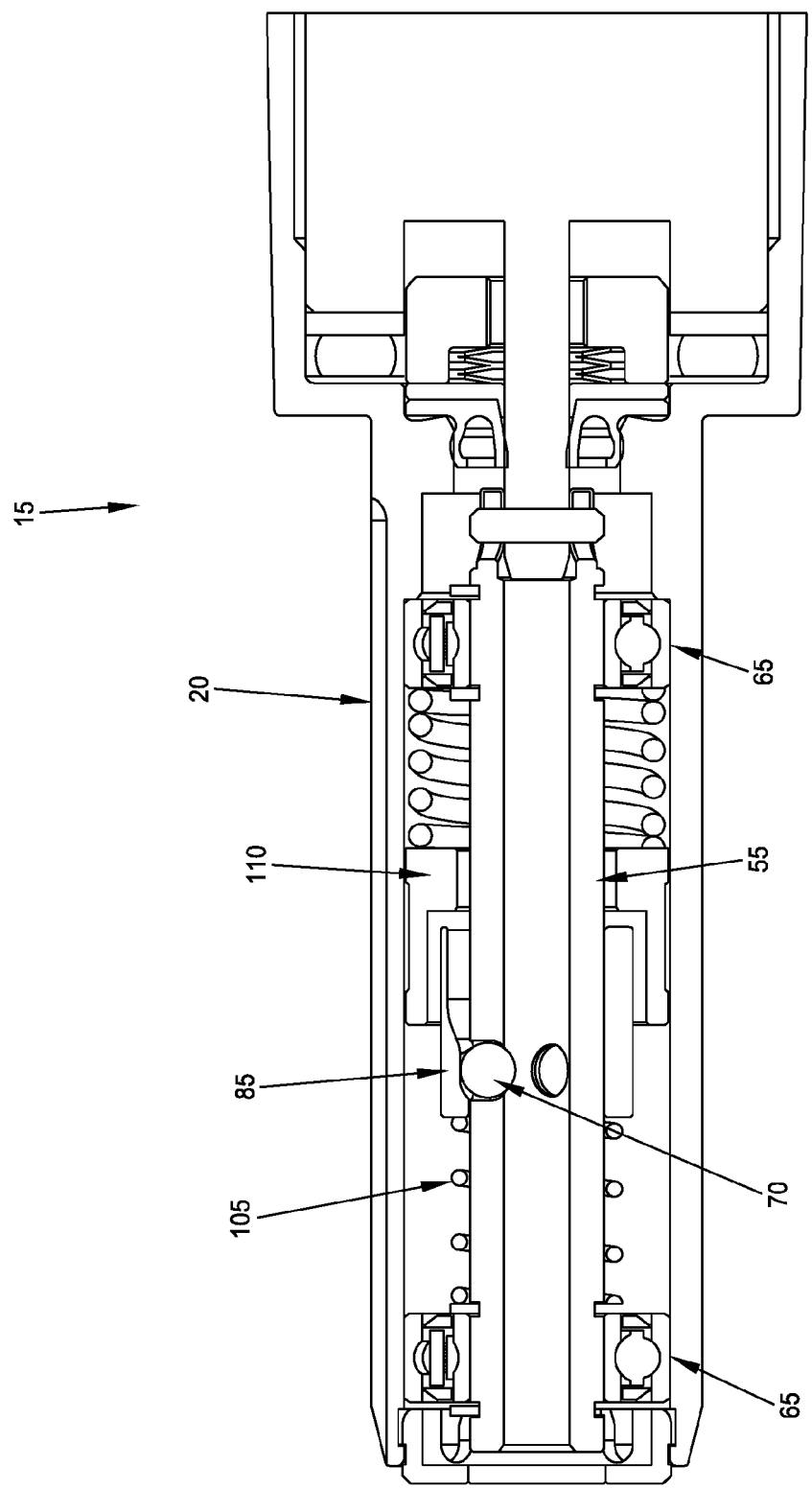

More particularly, and looking now at FIG. 6, at least one canted cam slot 120 is provided in distal mount 20. The at least one canted cam slot is canted with respect to the longitudinal axis of distal mount 20. The at least one canted cam slot 120 extends proximally and circumferentially between a distalmost surface 125 and a proximalmost surface 130. In one preferred form of the invention, the at least one canted cam slot 120 has a substantially straight configuration. In another preferred form of the invention, the at least one canted cam slot 120 has a substantially helical configuration. The at least one canted cam slot 120 also comprises a canted cam extension 135 which extends distally, and circumferentially, from proximalmost surface 130. At least one pin (or other element) 140 (FIG. 7), fixed to biasing collar 110, extends radially through the at least one canted cam slot 120 of distal mount 20, such that by moving the at least one pin 140 from its distalmost position within the at least one canted cam slot 120 (FIGS. 6 and 8), biasing collar 110 can be moved from its distalmost position (FIG. 4) to its proximalmost position (FIG. 9). Thus, by moving the at least one pin 140 proximally within the at least one canted cam slot 120, biasing collar 110 can be moved proximally within distal mount 20 so that cam element 85 is free to move proximally under the power of spring 105, whereby to cam the at least one collet ball 70 radially inwardly, whereby to intrude into central lumen 75 of collet sleeve 55 (e.g., to grip the shaft 50 of a working element 10 inserted into central lumen 75 of collet sleeve 55, or to prevent the shaft 50 of a working element 10 from being inserted into central lumen 75 of collet sleeve 55). In one preferred form of the invention, the at least one pin 140 is press fit or otherwise adhered to biasing collar 110.

Figure 10:
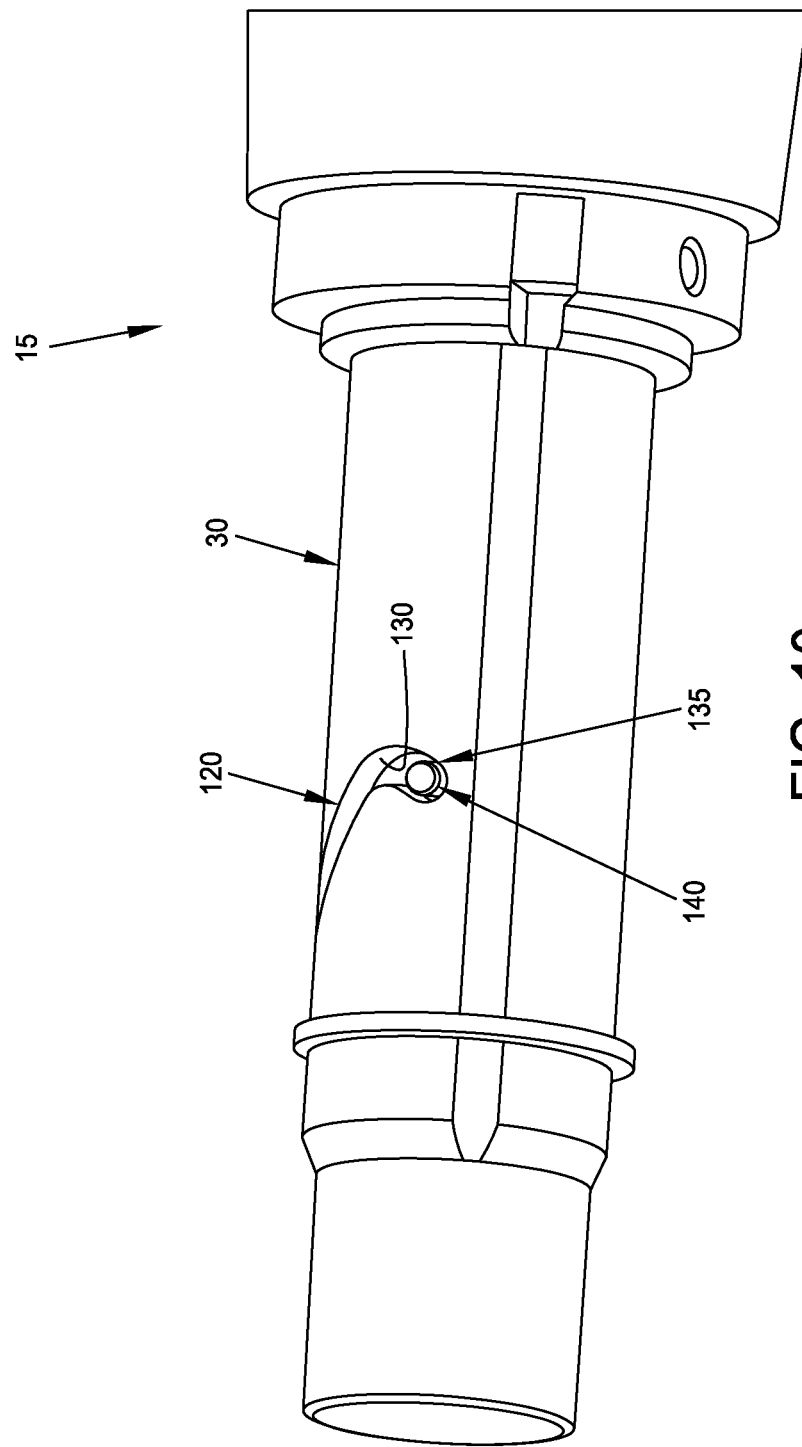
Figure 11:
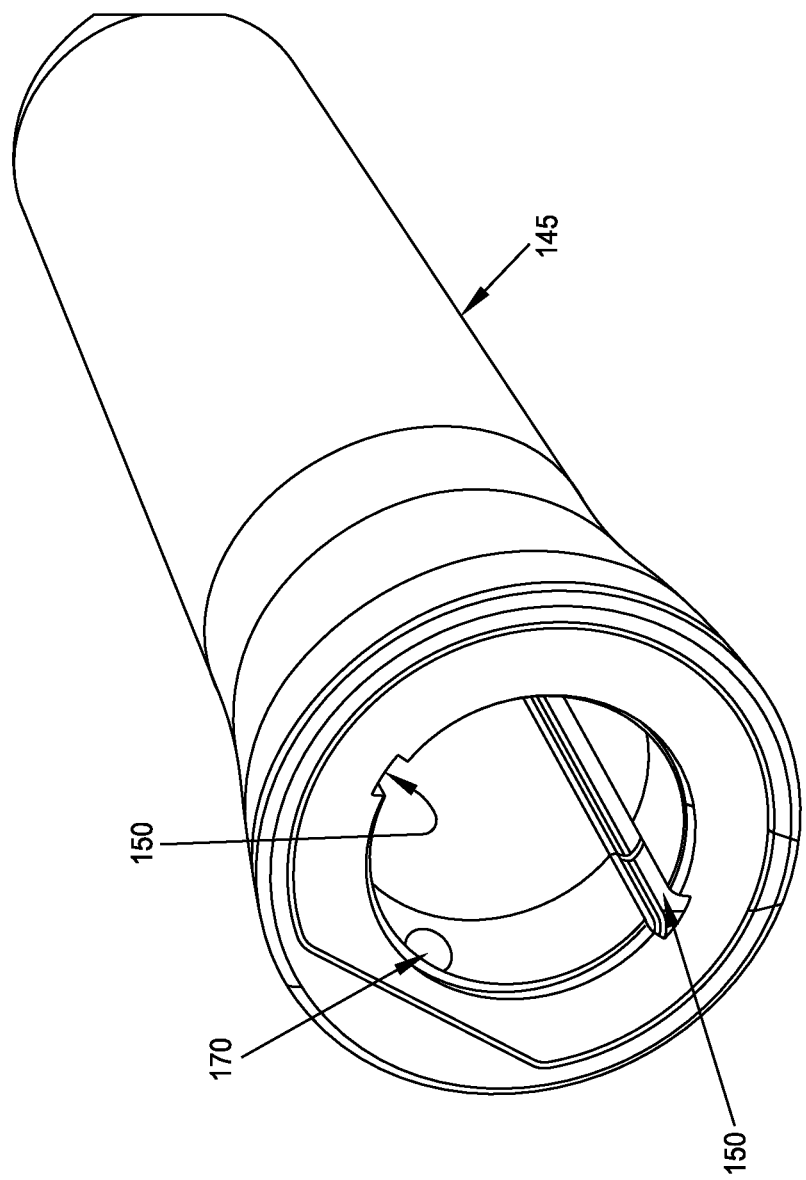

In addition, by moving the at least one pin 140 into canted cam extension 135 of the at least one canted cam slot 120 (FIG. 10), biasing collar 110 is releasably held proximally spaced from cam element 85 so that cam element 85 can cam the at least one collet ball 70 radially inwardly so as to grip the shaft 50 of a working element 10 (and also so that no frictional forces will be created between rotating cam element 85 and stationary biasing collar 110). In one preferred form of the invention, two canted cam slots 120, which may be diametrically-opposed to one another, are provided in mount 20, each having an associated canted cam extension 135, and two diametrically-opposed pins 140 extend radially outward from biasing collar 110 and through the two diametrically-opposed canted cam slots 120 (see FIG. 7).

Means are also provided for moving the at least one pin 140 within the at least one canted cam slot 120. More particularly, these means are provided by the aforementioned nosepiece assembly 22.

Looking now at FIGS. 2, 3, 7 and 11, nosepiece assembly 22 comprises means for supporting the shaft 50 of a working element 10 (e.g., distal tip 23, which may include bearings 142, see FIGS. 2 and 3) and a locking collar 145 (see FIGS. 7 and 11) disposed proximal to the aforementioned distal tip 23. Locking collar 145 is rotatable relative to distal mount 20 of handle assembly 15 when nosepiece assembly 22 is mounted to a handle assembly 15. In one preferred form of the invention, locking collar 145 and distal tip 23 rotate as a unit. In another preferred form of the invention, locking collar 145 is rotatable relative to distal tip 23. In either case, however, locking collar 145 is rotatable relative to distal mount 20 of handle assembly 15 when nosepiece assembly 22 is mounted to handle assembly 15. Note that where locking collar 145 is rotatable relative to distal tip 23, distal tip 23 is secured against rotation relative to distal mount 20, e.g., by the provision of a keying feature such as male-female connection, where the male feature is provided on one of the distal tip 23 and the distal mount 20, and the female feature is provided on the other of the distal tip 23 and the distal mount 20.

Locking collar 145 generally comprises at least one groove (or slot) 150 for receiving the radially-outermost portion of the at least one pin 140 when nosepiece assembly 22 is mounted on distal mount 20 of handle assembly 15. As a result, when locking collar 145 is rotated, the at least one pin 140 is also rotated, causing the at least one pin 140 to move proximally within the at least one canted cam slot 120 of distal mount 120, and hence causing biasing collar 110 to move proximally within distal mount 20 (and hence allowing cam element 85 to move proximally under the power of spring 105, whereby to cam the at least one collet ball 70 radially inwardly into the lumen 75 of collet sleeve 55). In one preferred form of the invention, where coupling assembly 45 comprises two pins 140 extending through two canted cam slots 120 of distal mount 120, nosepiece assembly 22 comprises two grooves (or slots) 150 for receiving the two diametrically-opposed pins 140. Where two pins 140, two canted cam slots 120, and two grooves (or slots) 150 are provided, each of the two pins 140, two canted cam slots 120, and two grooves (or slots) 150 may be diametrically-opposed from one another.

Figure 12:
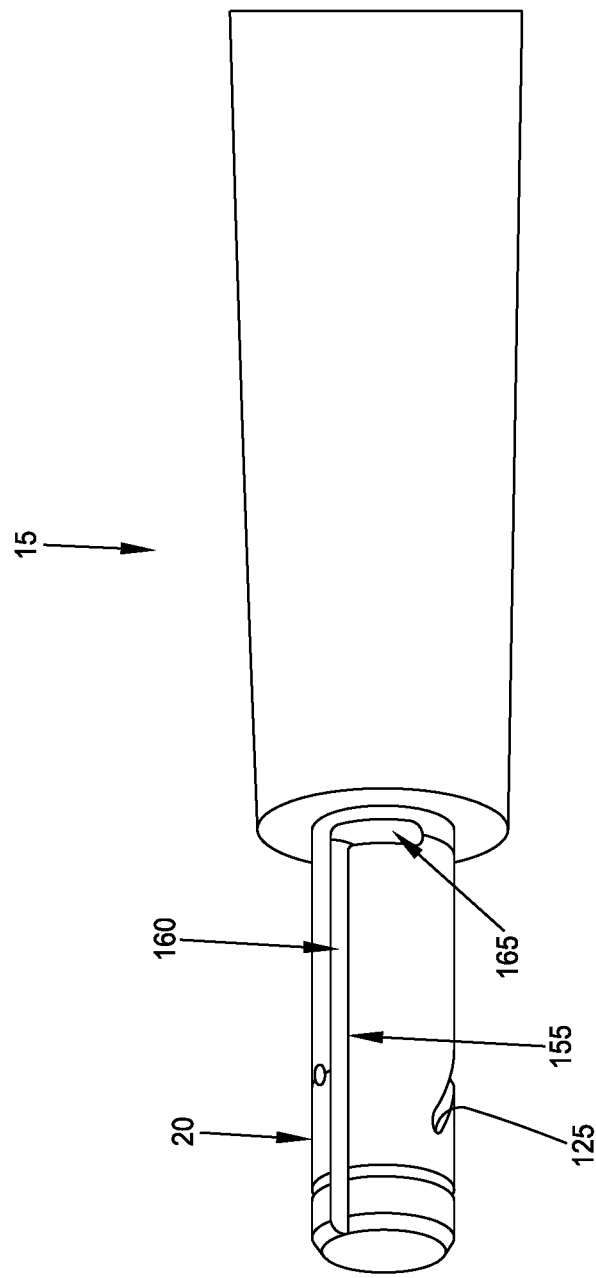

In order to releasably lock nosepiece assembly 22 to distal mount 20, distal mount 20 comprises an L-shaped groove (or slot) 155 (FIG. 12) having a longitudinally-extending section 160 and a circumferentially-extending section 165. Locking collar 145 of nosepiece assembly 22 comprises a ball 170 (FIG. 11) which is received in L-shaped groove (or slot) 155, i.e., ball 170 is received in longitudinally-extending section 160 when nosepiece assembly 22 is advanced onto distal mount 20 (or retracted off distal mount 20), and ball 170 is received in circumferentially-extending section 165 when locking collar 145 is rotated so as to (i) lock the shaft 50 of a working element 10 to coupling assembly 45 (and hence to handle assembly 15), or (ii) unlock the shaft 50 of a working element 10 from coupling assembly 45 (and hence from handle assembly 15). If desired, ball 170 can be replaced by a corresponding pin or finger or other element which is connected to locking collar 145 and is received in L-shaped groove (or slot) 155.

Thus it will be seen that nosepiece assembly 22 can be mounted to distal mount 20 of handle assembly 15 by aligning ball 170 of nosepiece assembly 22 with longitudinally-extending section 160 of L-shaped groove (or slot) 155 of distal mount 20, and then moving the two parts together until ball 170 is aligned with circumferentially-extending section 165 of L-shaped groove (or slot) 155 of distal mount 20. As this occurs, the at least one pin 140 of coupling assembly 45 is received in the at least one groove (or slot) 150 of locking collar 145, and as nosepiece assembly 22 is mounted to distal mount 20 of handle assembly 15, the at least one pin 140 of coupling assembly 45 is disposed at the distal end 125 of the at least one canted cam slot 120 of distal mount 20. At this point, coupling assembly 45 is in the position shown in FIG. 4 (i.e., unlocked).

Figure 13:
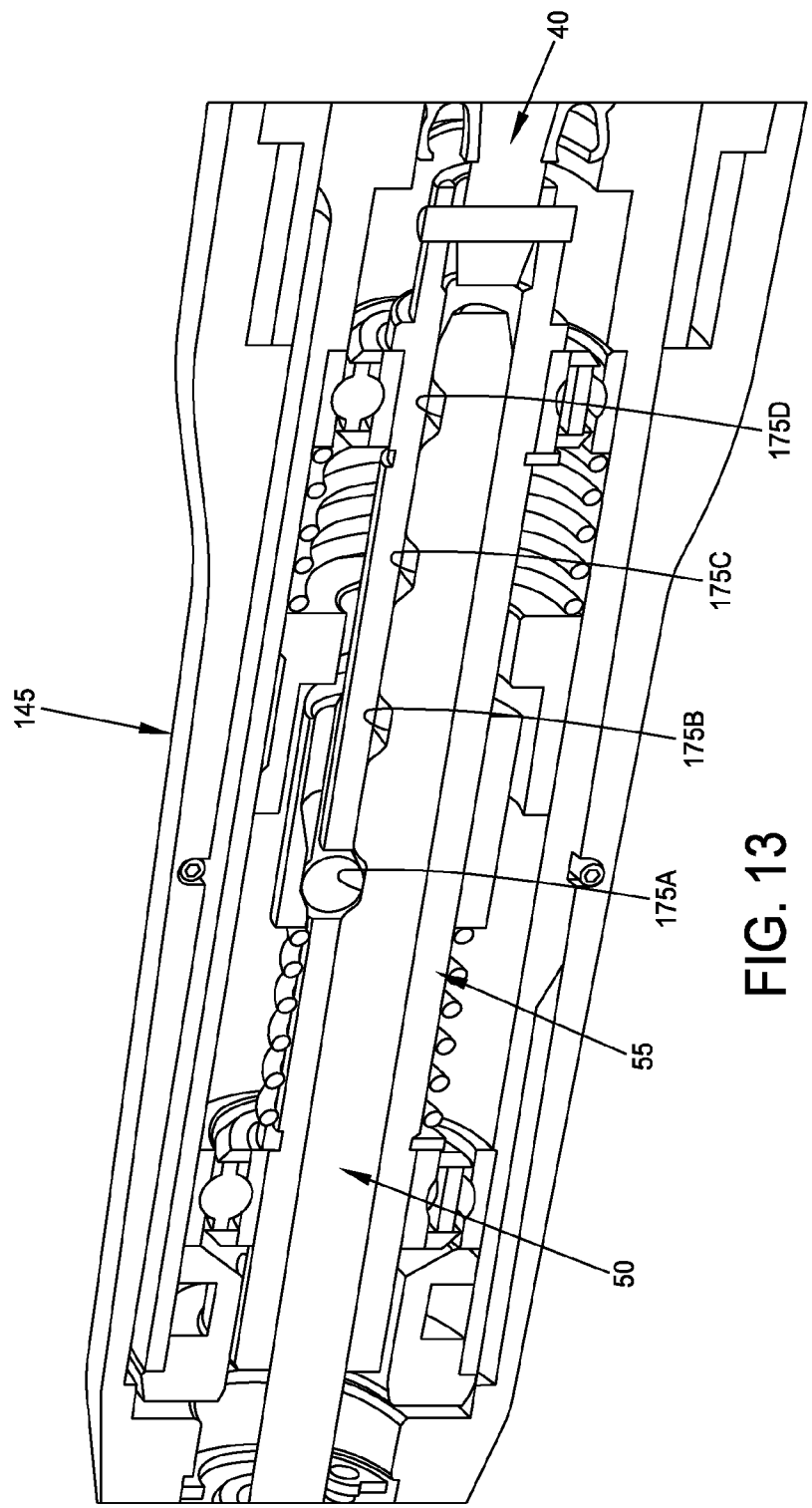

Thereafter, the shaft 50 of a working element 10 may be advanced into, or retracted from, central lumen 75 of collet sleeve 55, since biasing collar 110 will normally force cam element 85 distally, so that the at least one collet ball 70 is free to move radially outward in the at least one opening 60 in collet sleeve 55. The shaft 50 of a working element 10 can be advanced such that the at least one collet ball 70 is able to settle into at least one recess 175 (FIG. 13) formed in the shaft 50 of a working element 10. Note that in one preferred form of the invention, where three equally-circumferentially-spaced openings 60 and three collet balls 70 are provided, three equally-circumferentially-spaced recesses 175 are also provided, such that each equally-circumferentially-spaced recess 175 can receive one collet ball 70.

Locking collar 145 may then be rotated, whereby to cause the at least one pin 140 to move within the at least one canted cam slot 120, whereby to force biasing collar 110 proximally. As this occurs, cam element 85 is free to move proximally, whereby to force the at least one collet ball 70 radially inwardly, whereby to lock shaft 50 of working element (e.g., a drill bit or burr) 10 to coupling 45.

At the end of the rotation of locking collar 145, the at least one pin 140 settles into canted cam extension 135 of the at least one canted cam slot 120. With the at least one pin 140 settled into canted cam extension 135 of the at least one canted cam slot 120, biasing collar 110 is held proximally spaced from cam element 85, so that there is no frictional contact between biasing collar 110 (which is rotationally stationary) and cam element 85 (which rotates with collet sleeve 55).

At this point, motor 30 may be energized so as to rotate its shaft 40, whereby to rotate collet sleeve 55 of coupling assembly 45, and hence rotate working element 10 (which is releasably secured to collet sleeve 55). Working element 10 may then be used for its intended purpose, e.g., to drill or abrade bone.

Thereafter, when working element 10 is to be released from handle assembly 15, locking collar 145 of nosepiece assembly 22 is rotated again, but this time in the opposite direction, whereby to cause the at least one pin 140 to move out of canted cam extension 135 of the at least one canted cam slot 120, and then distally along the at least one canted cam slot 120, whereby to cause biasing collar 110 to move distally, such that cam element 85 also moves distally. As this occurs, cam element 85 allows the at least one collet ball 70 to move radially outwardly, whereby to free shaft 50 of working element 10 from handle assembly 15.

Note that in one preferred form of the invention, when the at least one pin 140 is in the at least one canted cam slot 120, the power of spring 115 alone is insufficient to drive biasing collar 110 distally (and hence insufficient to drive the at least one pin 140 distally, and hence insufficient to rotate locking collar 145 about distal mount 20). In this form of the invention, manual movement of locking collar 145 is required to drive biasing collar 110 distally (and hence to drive the at least one pin 140 distally, and hence to rotate locking collar 145 about distal mount 20).

However, in another form of the invention, when the at least one pin 140 is in the at least one canted cam slot 120, the power of spring 115 alone is sufficient to drive biasing collar 110 distally (and hence sufficient to drive the at least one pin 140 distally, and hence sufficient to rotate locking collar 145 about distal mount 20). In this form of the invention, manual motion of locking collar 145 is only necessary to move the at least one pin 140 out of canted cam extension 135 and into the at least one canted cam slot 120, and manual motion of locking collar 145 is not thereafter required to drive biasing collar 110 distally (and hence to drive the at least one pin 140 distally, and hence to rotate locking collar 145 about distal mount 20).

In one preferred form of the invention, the equally-circumferentially-spaced recesses 175 may be provided in sets (e.g., sets of three equally-circumferentially-spaced recesses), and multiple sets of the equally-circumferentially-spaced recesses 175 may be provided in axially-spaced locations along shaft 50 of working element 10, such that shafts of differing lengths may be accommodated. By way of example but not limitation, see FIGS. 3 and 13, which show four axially-spaced sets of three equally-circumferentially-spaced recesses 175 (i.e., 175A, 175B, 175C, 175D) formed in shaft 50 of working element 10.

If desired, the at least one pin 140 may be replaced by at least one other element, e.g., at least one ball. Where a ball is used in place of a pin, the ball may be retained in a pocket formed in biasing collar 110, and in another pocket formed in locking collar 145, with the ball extending through the at least one canted cam slot 120. However, the use of a pin offers significant advantages over the use of a ball, since (i) a pin can be press fit to biasing collar 110, which provides a fast and simple connection between biasing collar 110 and the pin; (ii) the height of a pin is independent of the width of the pin, whereas the "height" of a ball is the same as the "width" of the ball—so that as the "height" of the ball is increased to make a secure engagement with locking collar 145, the "width" of the ball must increase as well; and (iii) a pin generally makes a better camming contact with the at least one canted cam slot 120 than a ball. For at least these reasons, it is generally preferred to use a pin (rather than a ball) to connect biasing collar 110 to locking collar 145.

Figure 14:
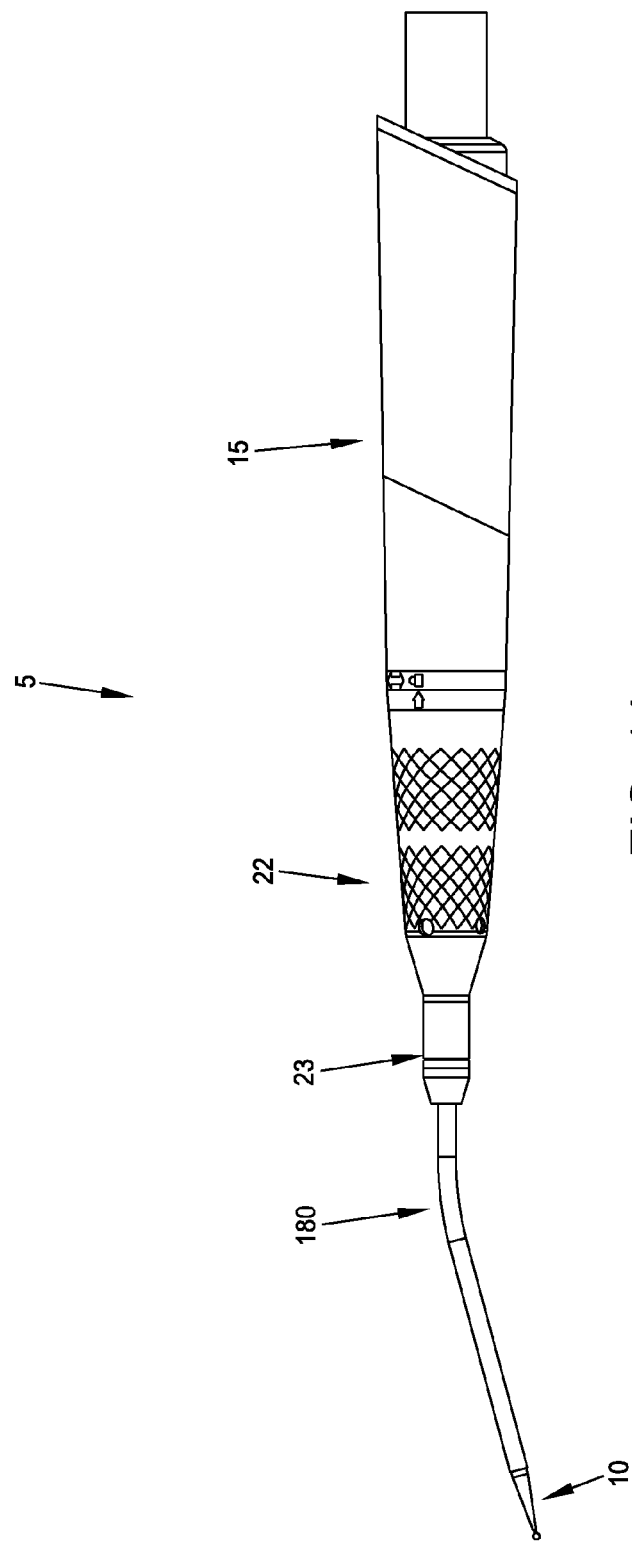
FIGS. 14 and 15 are schematic views showing another novel rotary tool provided in accordance with the present invention.
Figure 15:
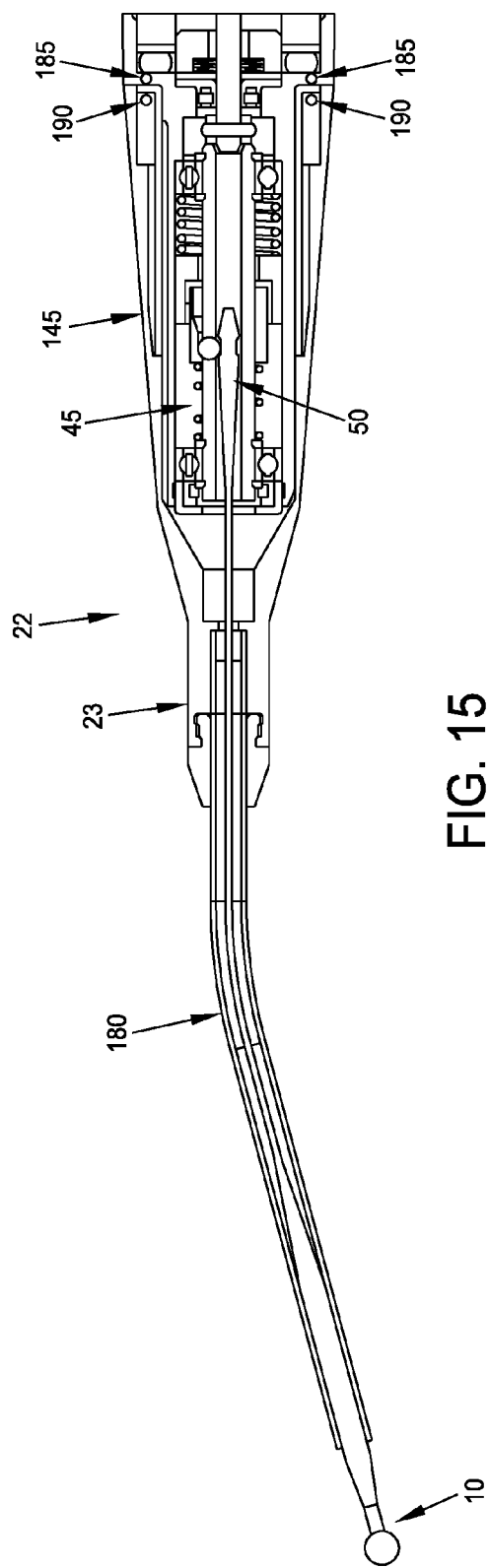
Figure 16:
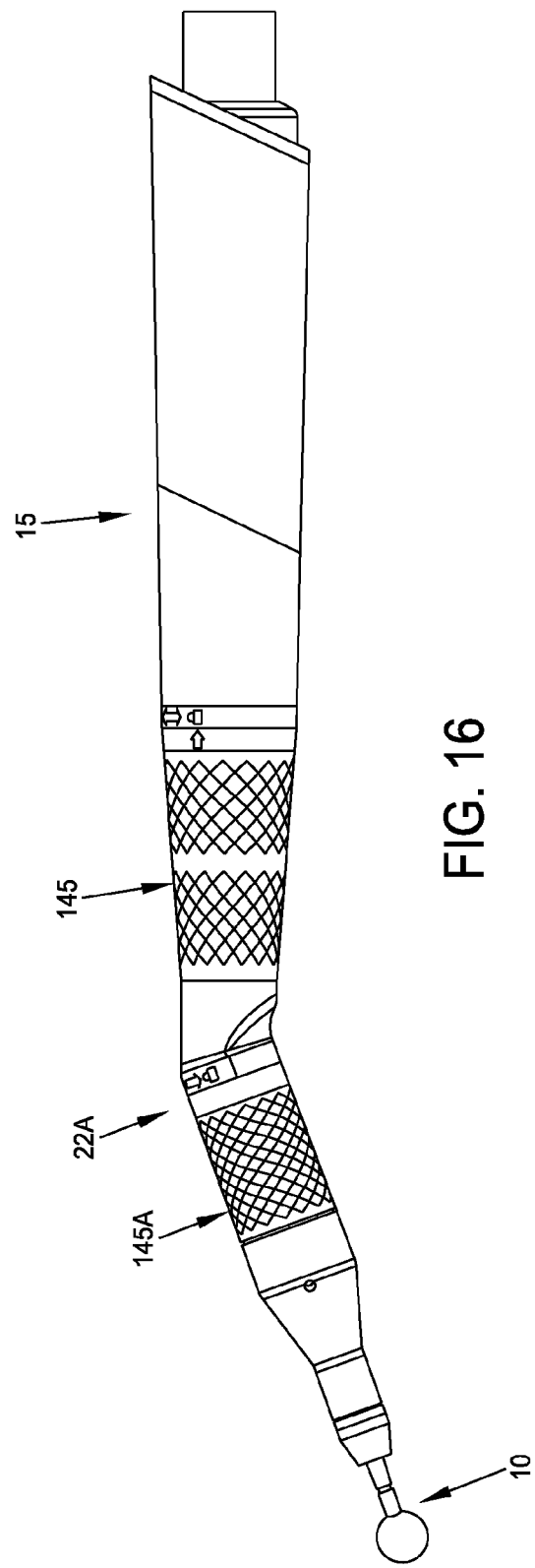
FIGS. 16 and 17 are schematic views showing still another novel rotary tool provided in accordance with the present invention.
Figure 17:
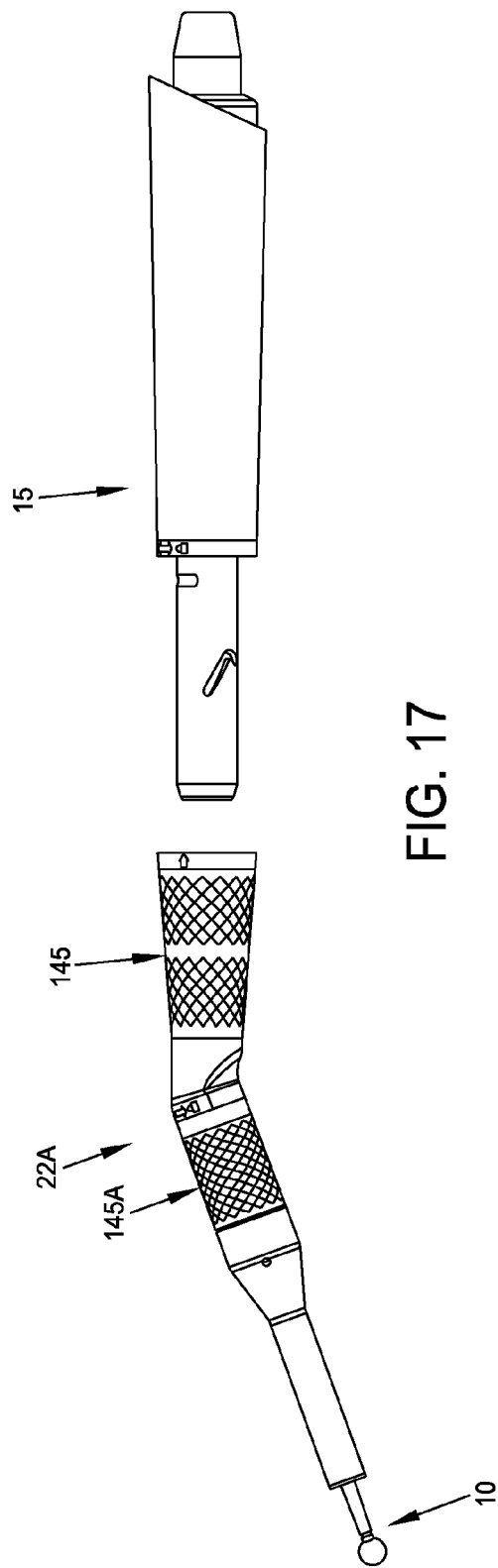
Figure 18:
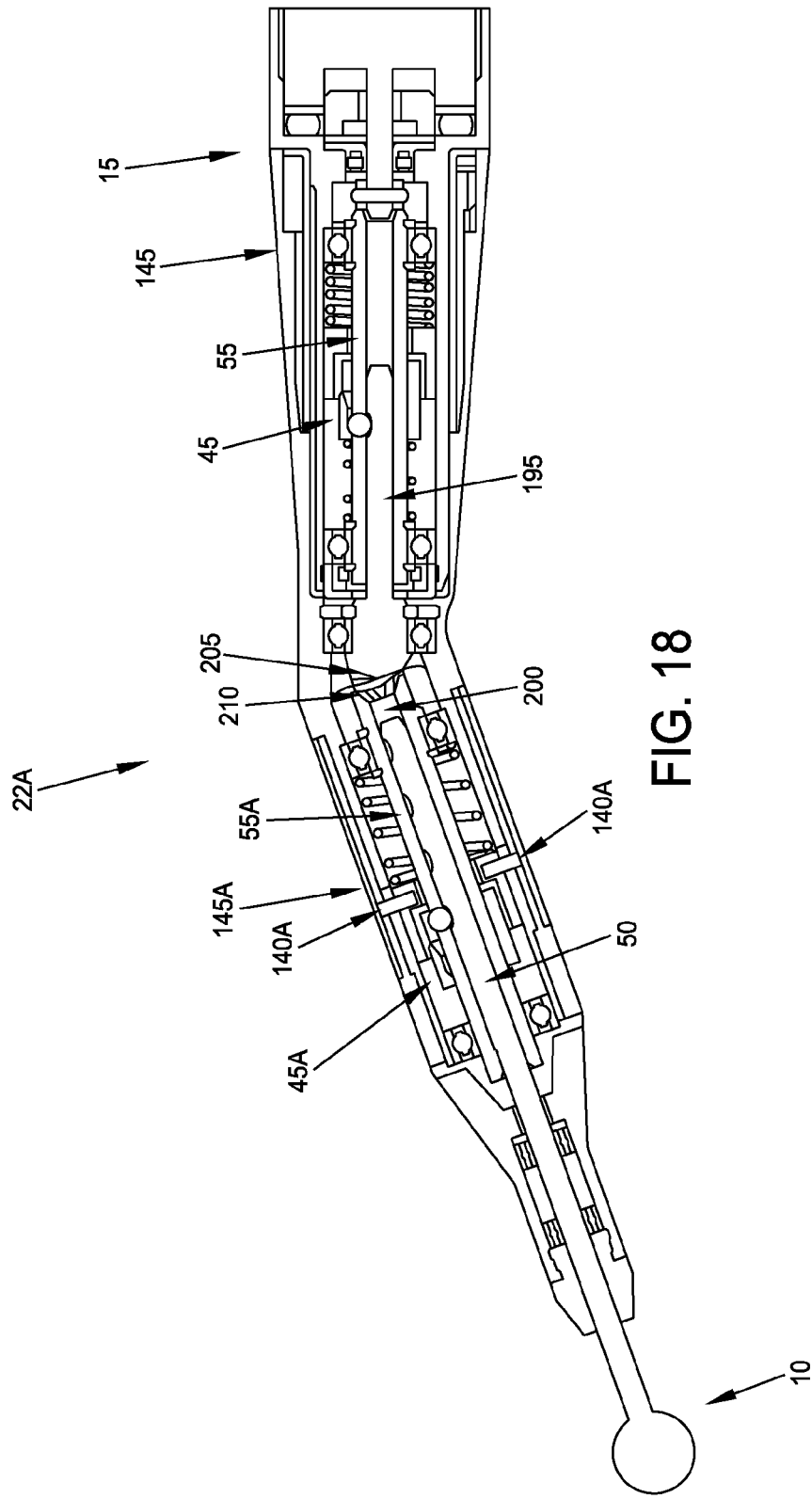
FIGS. 18 and 19 are schematic views showing construction details of the novel rotary tool shown in FIGS. 16 and 17.
Figure 19:
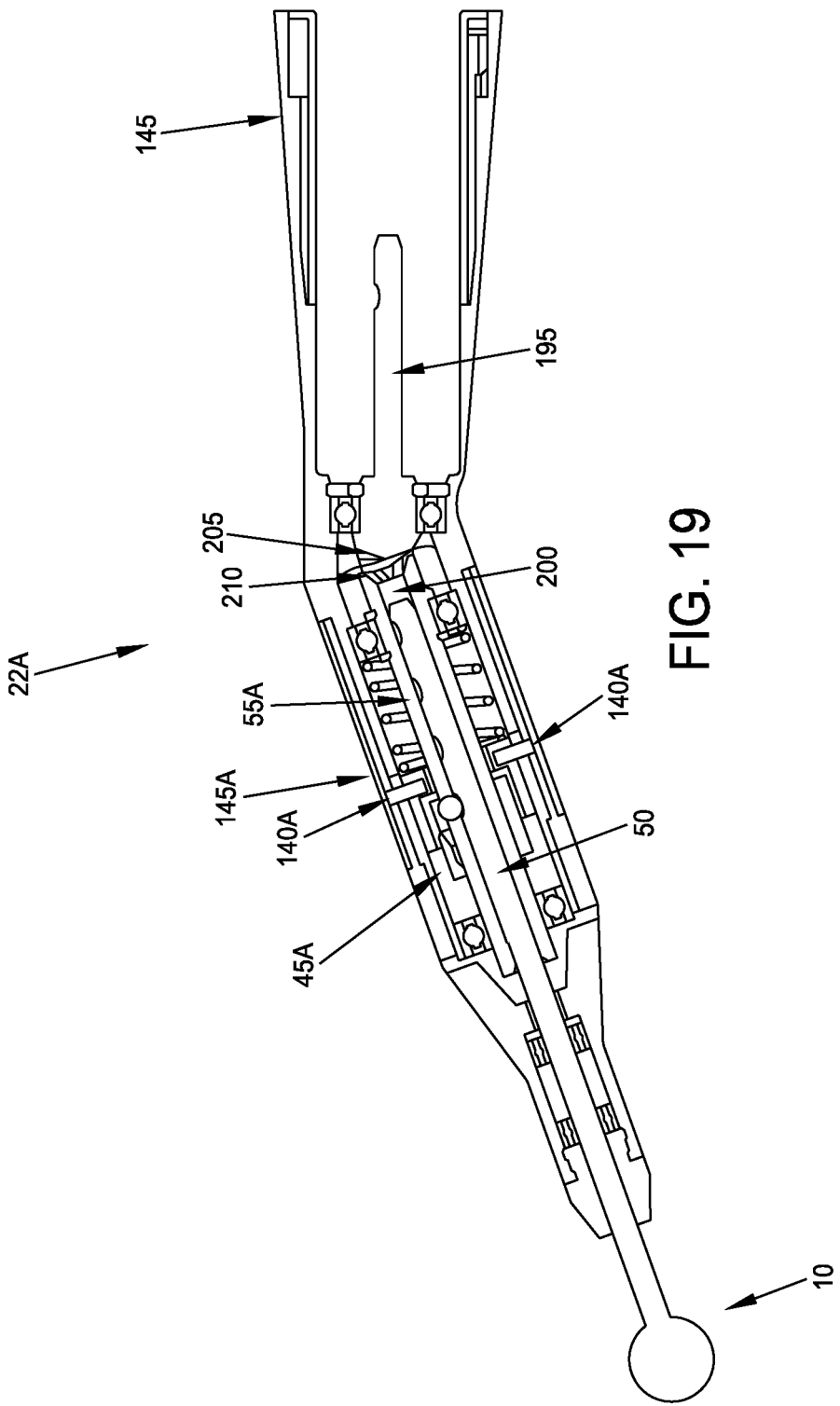
Figure 20:
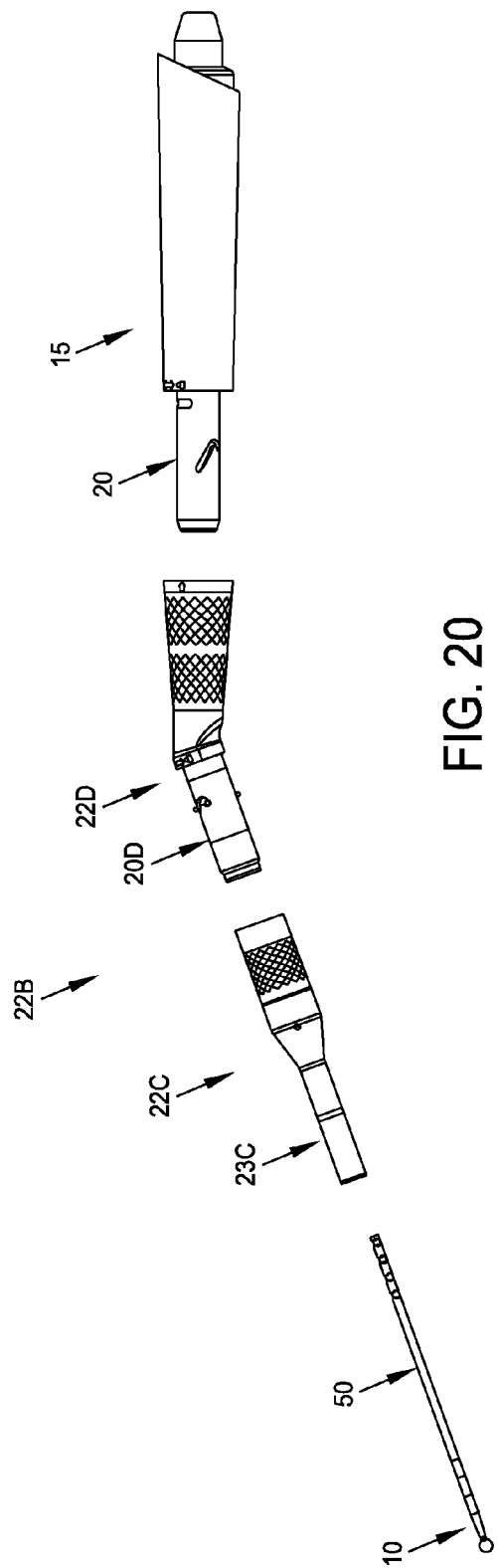
FIGS. 20-24 are schematic views showing yet another novel rotary tool provided in accordance with the present invention.
Figure 21:
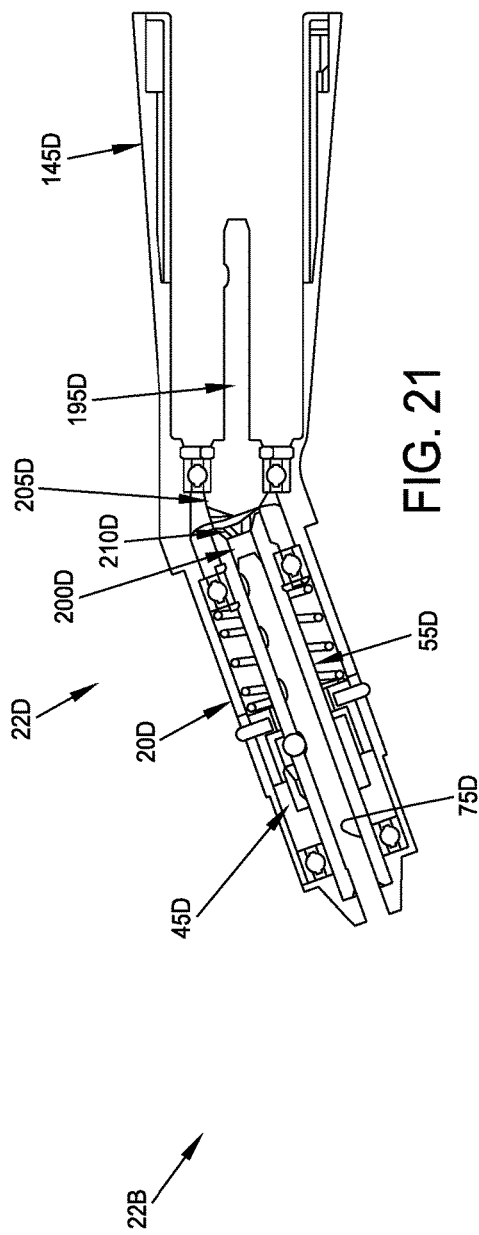
Figure 22:
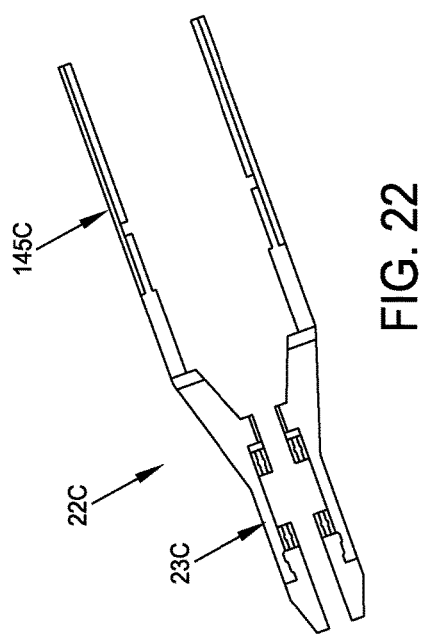
Figure 23:
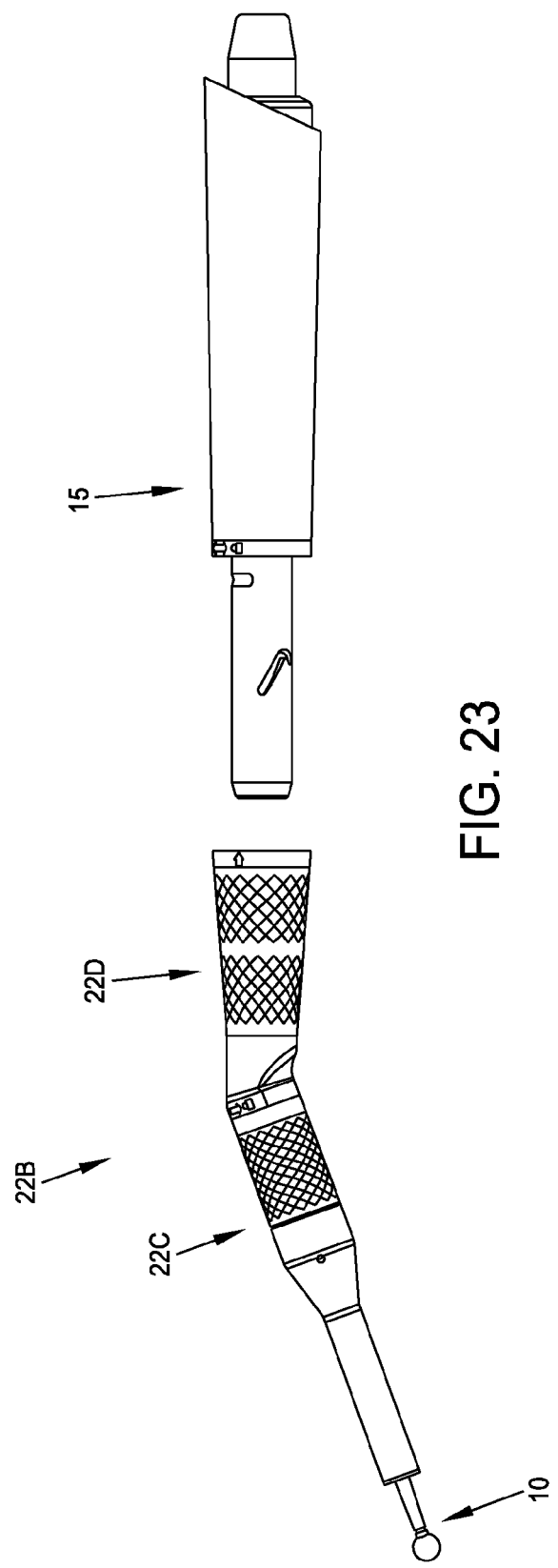
Figure 24:
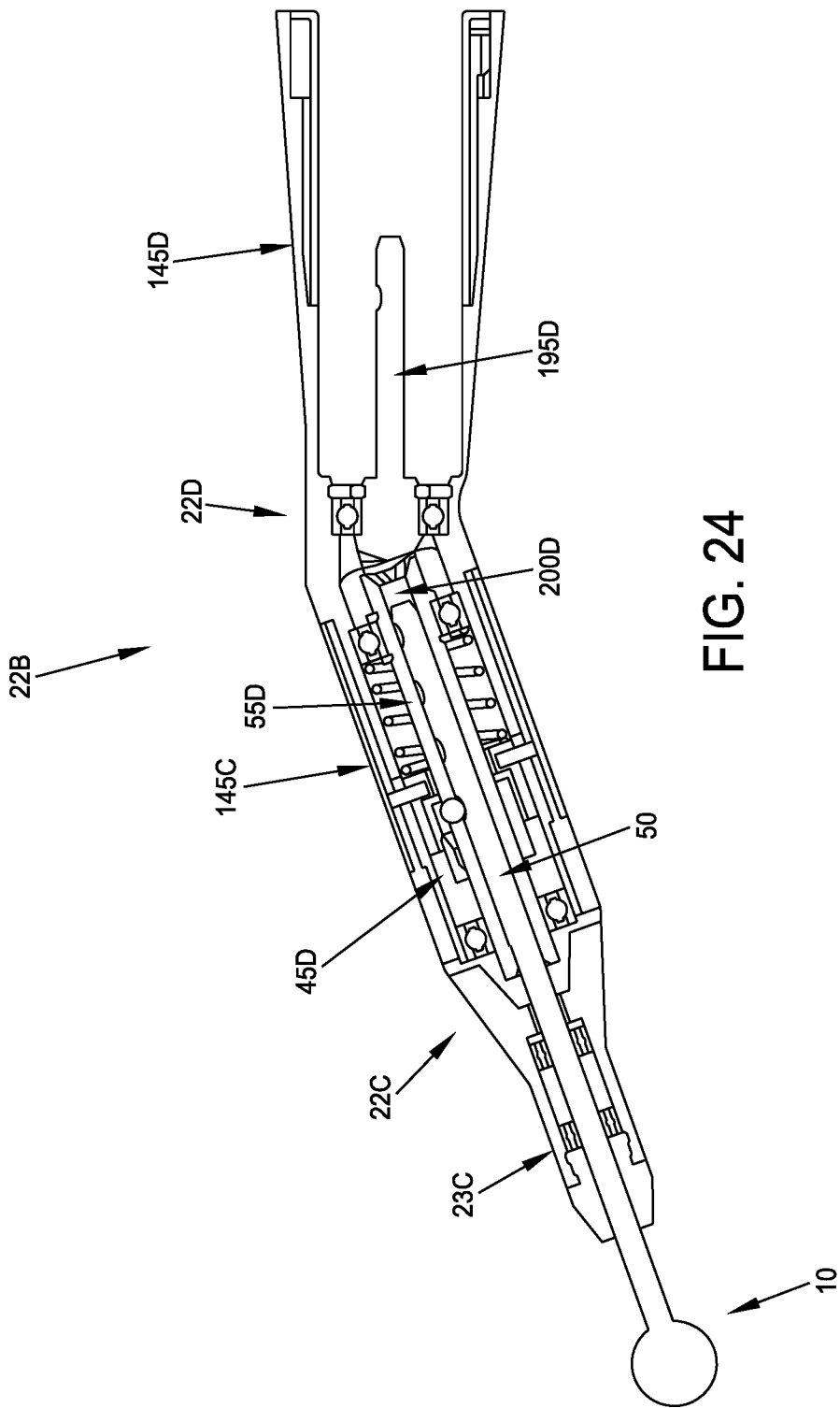

As seen in FIGS. 14 and 15, distal tip 23 of nosepiece assembly 22 may include a curved extension 180 for rotatably receiving a working element 10 having a flexible shaft. Note that where nosepiece assembly 22 comprises a curved extension 180 and working element 10 comprises a flexible shaft, it is common to drive the working element 10 at a slower speed than where the working element 10 is substantially straight and rigid, in order to reduce the stress on the flexible shaft of the working element 10 and thereby help preserve its working life. To this end, it can be advantageous to provide handle assembly 15 with means for detecting when distal tip 23 of nosepiece assembly 22 comprises a curved extension 180. In one preferred form of the invention, and looking now at FIG. 15, handle assembly 15 can include a plurality of Hall sensors 185, and nosepiece assembly 22 (comprising a distal tip 23 having a curved extension 180) can include a plurality of magnets 190, such that handle assembly 15 can detect when a nosepiece assembly 22 (of the sort comprising a distal tip 23 having a curved extension 180) is mounted to handle assembly 15 (and hence reduce the operating speed of motor 30 so as to preserve the working life of the working element 10).

Note that, if desired, and as shown in FIGS. 14 and 15, bearings 142 may be omitted from nosepiece assembly 22, and shaft 50 of a working element 10 may be supported by a simple sliding contact made directly against nosepiece assembly 22.

As noted above, in accordance with the present invention, nosepiece assembly 22 is configured as a separate element from handle assembly 15, and is mountable to, and fully removable from, distal mount 20 of handle assembly 15.

It should be appreciated that, by providing nosepiece assembly 22 as a fully-separable element from handle assembly 15, it is possible to provide a wide variety of different nosepiece assemblies 22, with each nosepiece assembly 22 being configured for a different purpose (e.g., for performing a different task, for supporting a differently-configured working element, etc.), with each nosepiece assembly 22 comprising a distal tip 23 for slidably supporting a working tool 10 and a locking collar 145 for engaging the at least one pin 140 of a coupling assembly 45 disposed in distal mount 20 of handle assembly 15.

Significantly, the nosepiece assembly may be configured to provide an angled shaft configuration. In this form of the invention, and looking now at FIGS. 16-19, there is provided a nosepiece assembly 22A which comprises the aforementioned locking collar 145 for engaging the at least one pin 140 of coupling assembly 45 of handle assembly 15, and the aforementioned distal tip 23 for slidably receiving the shaft 50 of a working tool 10. However, in this form of the invention, nosepiece assembly 22A also comprises a second coupling assembly 45A, a second locking collar 145A, and a pair of shafts 195, 200. Second coupling assembly 45A is substantially the same as the coupling assembly 45 previously disclosed, except that it is disposed in nosepiece assembly 122A distal to locking collar 145. Second locking collar 145A is provided on nosepiece assembly 22A and is configured to engage the at least one pin 140A of second coupling assembly 45A, whereby to lock or unlock a working element 10 to second coupling assembly 45A. Shaft 200 is received by the aforementioned coupling assembly 45 in distal mount 20 of handle assembly 15 when nosepiece assembly 22 is mounted to handle assembly 15, such that when locking collar 145 is rotated, shaft 195 is mechanically connected (via coupling assembly 45 in distal mount 20 of handle assembly 15) to drive shaft 40 of high speed motor 30. Shaft 195 includes a beveled gear 205 at its distal end. Shaft 200 is connected to collet sleeve 55A of coupling assembly 45A, and includes a beveled gear 210 at its proximal end which is rotatably connected to gear 205 of shaft 195, such that when shaft 40 of high speed motor 30 is rotated, collet sleeve 55A is also rotated (i.e., via the intervening collet sleeve 55 of coupling assembly 45 of handle assembly 15, and via the intervening shaft 195 and shaft 200 of nosepiece assembly 22). In this form of the invention, second coupling 45A of nosepiece assembly 22 releasably receives the shaft 50 of working element 10. Second locking collar 145A of nosepiece assembly 22A is used to selectively lock/unlock the shaft 50 of a working element 10 to second coupling assembly 45A of nosepiece 22A.

Significantly, by forming nosepiece assembly 22A so that the longitudinal axis of shaft 195 is set at an angle to the longitudinal axis of collet sleeve 55A of second coupling 45A, "off-angle" drilling can be effected without requiring the use of a nosepiece assembly having a curved extension 180 and a drill bit having a flexible shaft. This is a significant advance in the art, since it allows high speed "off angle" drilling or burring to be effected for prolonged periods of time without unduly limiting the life of working element 10.

If desired, the angled shaft nosepiece assembly 22A (FIGS. 16-19) can be provided as a single assembly, which mounts and dismounts as a unit from distal mount 20 of handle assembly 15.

Alternatively, if desired, and looking now at FIGS. 20-24, there is shown a nosepiece assembly 22B which comprises (i) a nosepiece assembly 22C, and (ii) a handle assembly adapter 22D, wherein nosepiece assembly 22C and handle assembly adapter 22D are separable from one another (FIGS. 20-22), but may be connected together, e.g., at the time of manufacture, at the time of use, etc. (FIGS. 23 and 24), so as to together form the complete nosepiece assembly 22B. The nosepiece assembly 22B may be an angled shaft nosepiece assembly.

In this form of the invention, nosepiece assembly 22C may be identical to the aforementioned nosepiece assembly 22, i.e., nosepiece assembly 22C comprises a distal tip 23C and a locking collar 145C.

In this form of the invention, handle assembly adapter 22D may comprise a distal mount 20D containing a coupling assembly 45D which receives the shaft 50 of a working element 10 and is activated by locking collar 145C of nosepiece assembly 22C. And in this form of the invention, handle assembly adapter 22D may comprise a shaft 195D for being received in coupling assembly 45 in distal mount 20 of handle assembly 15, and a shaft 200D for transferring the rotation of shaft 195D to collet sleeve 55D of coupling assembly 45D disposed in handle assembly adapter 22D (and hence transferring rotation of shaft 195D to the shaft 50 of a working element 10 disposed in central lumen 75D of collet sleeve 55D). In this form of the invention, handle assembly adapter 22D comprises a locking collar 145D for actuating coupling assembly 45 in distal mount 20 of handle assembly 15. It will also be appreciated that in this form of the invention, handle assembly adapter 22D is releasably secured to distal mount 20 of handle assembly 15 by loading locking collar 145D of handle assembly adapter 22D onto distal mount 20 of handle assembly 15 in a manner analogous to the manner in which nosepiece assembly 22 is mounted onto distal mount 20 of handle assembly 15, and in this form of the invention, nosepiece assembly 22C is releasably secured to distal mount 20D of handle assembly adapter 22D by loading locking collar 145C of nosepiece assembly 22C onto distal mount 20D of handle assembly adapter 22D in a manner analogous to the manner in which nosepiece assembly 22 is mounted onto distal mount 20 of handle assembly 15.

Thus it will be seen that, in this form of the invention, nosepiece assembly 22B comprises a first mounting mechanism comprising a locking collar 145D for securing handle assembly adapter 22D to distal mount 20 of handle assembly 15, and a second mounting mechanism for securing nosepiece assembly 22C to distal mount 20D of handle assembly adapter 22D. However, it should also be appreciated that, if desired, an alternative mounting mechanism may be used to secure handle assembly adapter 22D to distal mount 20 of handle assembly 15 (while still using a locking collar 145C to secure nosepiece assembly 22C to handle assembly adapter 22D); and/or an alternative mounting mechanism may be used to secure nosepiece assembly 22C to handle assembly adapter 22D (while still using the aforementioned locking collar 145D to secure handle assembly adapter 22D to distal mount 20 of handle assembly 15).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A surgical device comprising:
   a handle assembly comprising a rotatable drive shaft;
   a removable handle assembly adapter for connection to said handle assembly, said removable handle assembly adapter comprising a rotatable transmission shaft for connection to said rotatable drive shaft of said handle assembly; and
   a removable nosepiece assembly for connection to said removable handle assembly adapter and for selectively securing the shaft of a working element to said rotatable transmission shaft of said removable handle assembly adapter;
   wherein said removable handle assembly adapter and said removable nosepiece assembly each comprise a locking collar; and
   wherein said removable handle assembly adapter and said handle assembly each comprise a connector assembly, said connector assembly comprising:
      a housing comprising an opening;
      a collet sleeve disposed within said opening and connected to an input shaft, said collet sleeve comprising a lumen for receiving an output shaft;
      a locking element movable relative to said collet sleeve between (i) a locked position in which said output shaft is secured to said collet sleeve, and (ii) an unlocked position in which said output shaft is not secured to said collet sleeve; and
      a cam element movable relative to said collet sleeve between (i) a first position in which said locking element is free to assume its said unlocked position, and (ii) a second position in which said cam element cams said locking element into said locked position;
   such that movement of said locking collar causes said cam element to move between said first position and said second position.

2. A surgical device according to claim 1 wherein said connector assembly of said handle assembly is configured to receive said rotatable transmission shaft of said removable handle assembly adapter in order to secure said rotatable transmission shaft of said removable handle assembly adapter to said rotatable drive shaft of said handle assembly, and said connector assembly of said removable handle assembly adapter is configured to receive a shaft of a working element, in order to secure the shaft of the working element to said collet sleeve of said connector assembly of said removable handle assembly adapter.

3. A surgical device according to claim 1 wherein said housing comprises an L-shaped slot, and further wherein said locking collar comprises an follower for extending into said L-shaped slot.

4. A surgical device according to claim 3 wherein said L-shaped slot comprises a first leg and a second leg, and further wherein said first leg extends longitudinally along said housing and said second leg extends circumferentially along said housing.

5. A surgical device according to claim 4 wherein said follower is disposed in said first leg of said L-shaped slot when said locking collar is being mounted onto, or dismounted from, said housing, and further wherein said follower is disposed in said second leg of said L-shaped slot when said locking collar is rotated so as to cause said biasing collar to move said cam element into said second position.

6. A surgical device according to claim 1 further comprising a working element comprising a shaft.

7. A surgical device comprising:
   a handle assembly comprising
   a powered drive shaft; and
   a first connector assembly;
      a removable nosepiece assembly for connection to said handle assembly, said removable nosepiece assembly comprising:
      a first shaft with a first shaft engagement portion for connection to said powered drive shaft of said handle assembly;
      a second shaft with a second shaft engagement portion for connection to the shaft of a working element; and
      a second connector assembly;
      wherein each of said first and second connector assemblies comprises:
         a housing comprising an opening;
         a collet sleeve disposed within said opening and connected to an input shaft, said collet sleeve comprising a lumen for receiving an output shaft;
         a locking element movable relative to said collet sleeve between (i) a locked position in which the output shaft is secured to said collet sleeve, and (ii) an unlocked position in which the output shaft is not secured to said collet sleeve;
         a cam element movable relative to said collet sleeve between (i) a first position in which said locking element is free to assume its said unlocked position, and (ii) a second position in which said cam element cams said locking element into said locked position; and
         a locking collar mounted to said housing such that rotation of said locking collar causes said cam element to move into said second position.

* * * * *